United States Patent [19]

Buchanan

[11] Patent Number: 5,097,832

[45] Date of Patent: Mar. 24, 1992

[54] SYSTEM AND METHOD FOR PREVENTING FALSE PACEMAKER PVC RESPONSE

[75] Inventor: Stuart W. Buchanan, Saugus, Calif.

[73] Assignee: Siemens-Pacesetter, Inc., Sylmar, Calif.

[21] Appl. No.: 491,385

[22] Filed: Mar. 9, 1990

[51] Int. Cl.⁵ .................................. A61N 1/365
[52] U.S. Cl. .................................. 128/419 PG
[58] Field of Search ....................... 128/419 PG

[56] References Cited

U.S. PATENT DOCUMENTS

| | | | |
|---|---|---|---|
| 4,173,230 | 11/1979 | Digby | 128/419 PG |
| 4,552,154 | 11/1985 | Hartlaub | 128/419 PG |
| 4,554,920 | 11/1985 | Baker, Jr. et al. | 128/419 PG |
| 4,554,922 | 11/1985 | Prystowsky et al. | 128/419 PG |
| 4,712,555 | 12/1987 | Thornander et al. | 128/419 PG |
| 4,788,980 | 12/1988 | Mann et al. | 128/419 PG |
| 4,790,317 | 12/1988 | Davies | 128/419 D |

Primary Examiner—William E. Kamm
Assistant Examiner—Kennedy J. Schaetzle
Attorney, Agent, or Firm—Bryant R. Gold; Lisa P. Weinberg; Malcolm J. Romano

[57] ABSTRACT

An implantable pacemaker having means for detecting and responding to a premature ventricular contraction (PVC), also includes circuit means for minimizing the likelihood of sensing a PVC when in fact a PVC has not occurred. The circuit means latches the occurrence of any atrial events sensed during the relative atrial refractory period of the pacemaker, whether such atrial events are noise or an early P-wave; and, in response to such latching, disables the PVC detection circuit until certain prescribed events occur, whereupon the PVC detection circuit is re-enabled. The prescribed events that re-enable the PVC detection circuit after it has been disabled include, e.g., the occurrence of a ventricular pulse or sensed R-wave. Further, in the event a PVC is detected and a desired PVC response is invoked, an additional circuit means automatically terminates the PVC response in the event the PVC response becomes stuck.

21 Claims, 10 Drawing Sheets

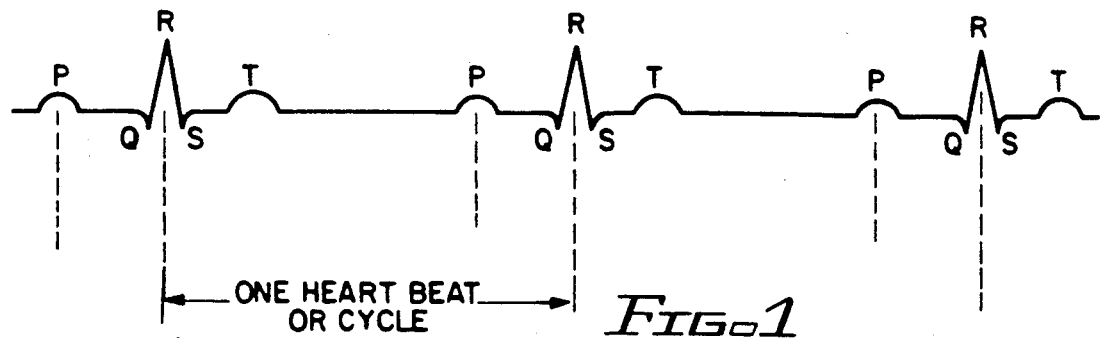
FIG. 1
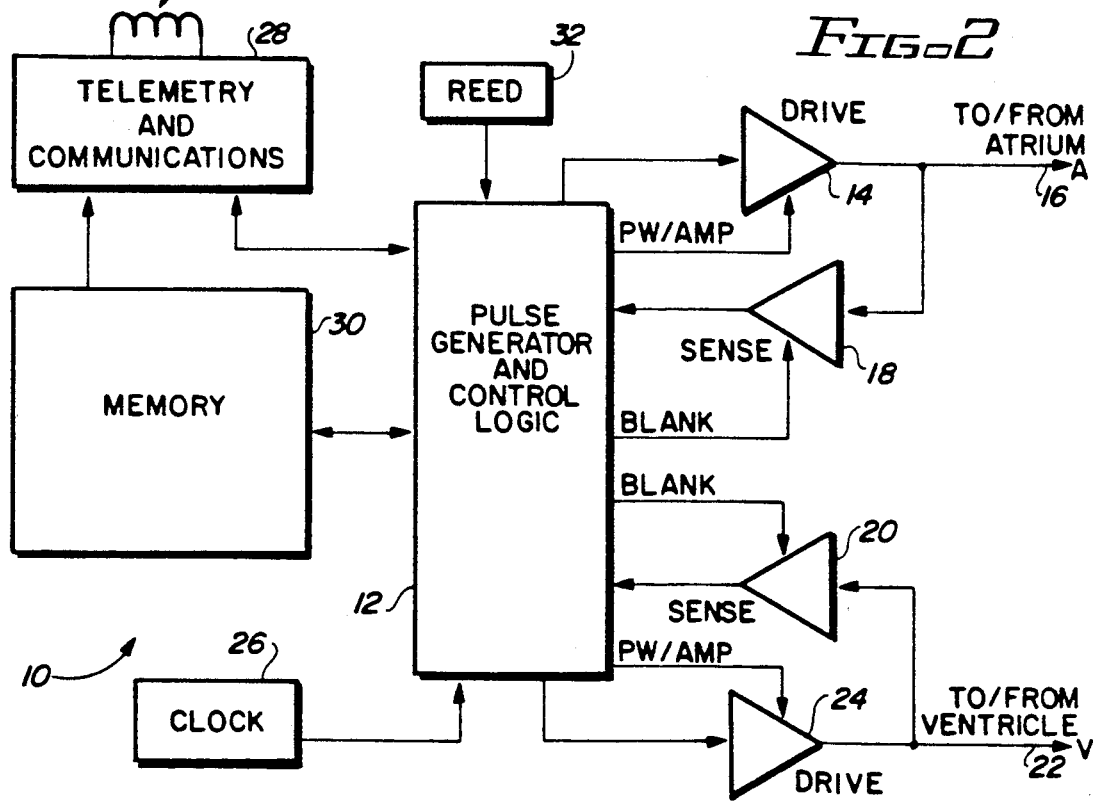
FIG. 2
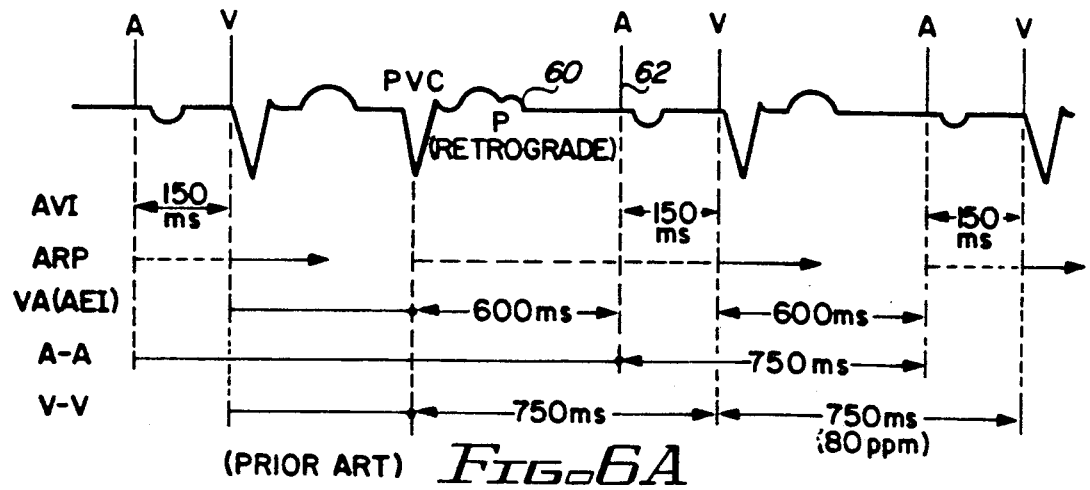
(PRIOR ART) FIG. 6A

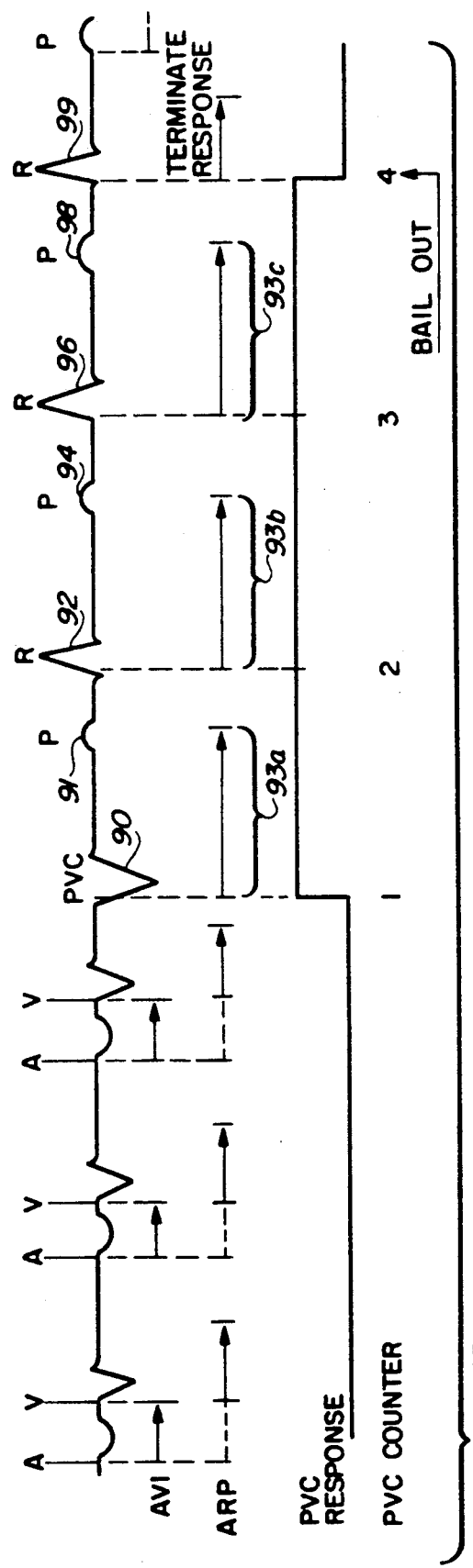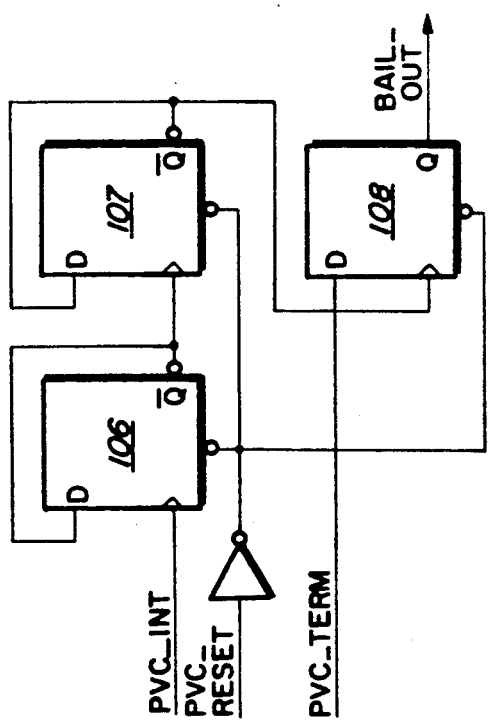

NOTE: P-WAVES 145a, 145b, AND 145c OCCUR DURING + PVARP RESPONSE AND ARE NOT DETECTED.

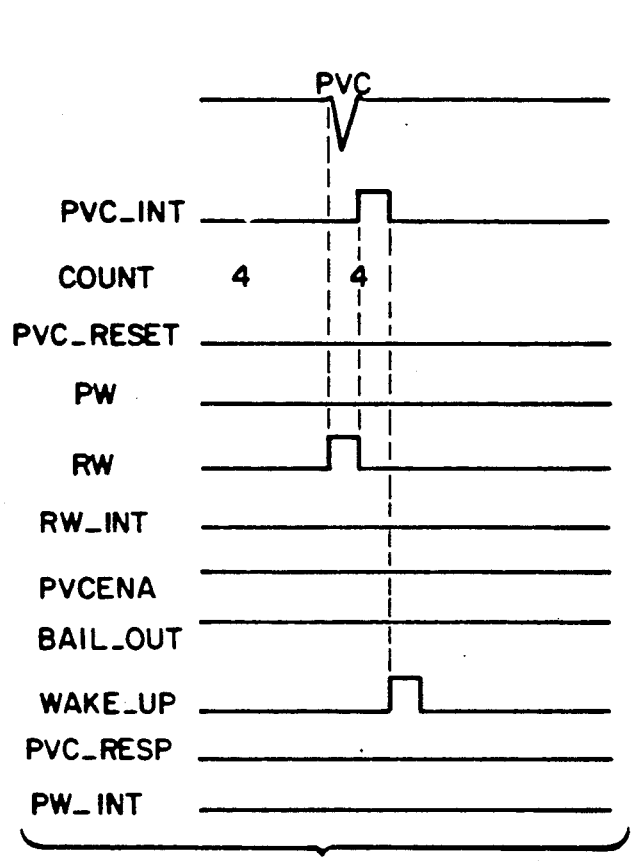
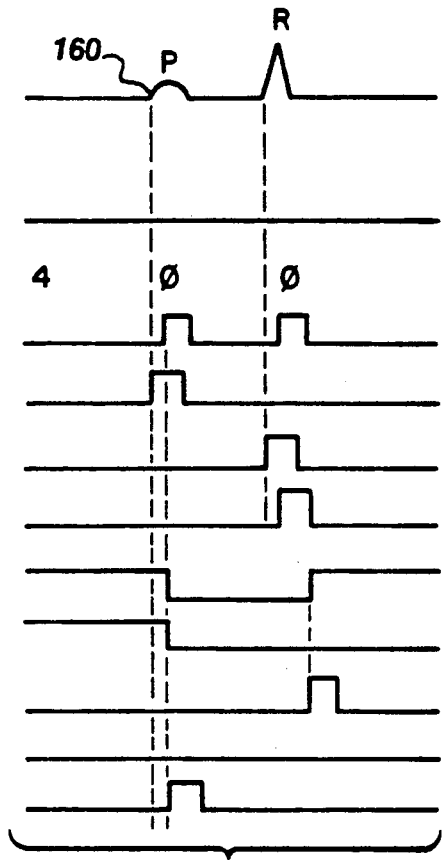
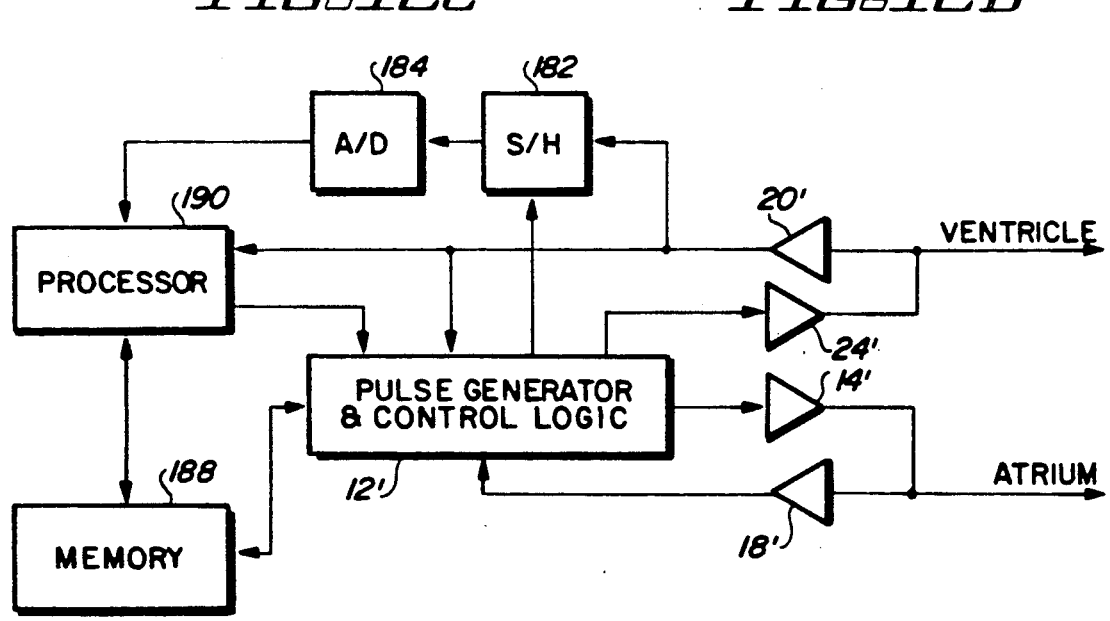

SYSTEM AND METHOD FOR PREVENTING FALSE PACEMAKER PVC RESPONSE

BACKGROUND OF THE INVENTION

This invention relates to cardiac pacemakers, and more particularly to implantable programmable cardiac pacemakers that respond to the occurrence of a premature ventricular contraction (PVC) in a prescribed manner. Specifically, a pacemaker in accordance with the present invention minimizes the likelihood that a PVC response is inappropriately triggered. Moreover, when a PVC response is provided, it is designed to reduce the likelihood that a pacemaker mediated tachycardia (PMT) will be triggered, or that the pacemaker will otherwise be prevented from efficiently performing its intended function.

In order to efficiently perform its function of a pump, the heart must maintain a natural AV synchrony. The term "AV synchrony" relates to the sequential timing relationship that exists between the contractions of the atria and the ventricles. In a given heart cycle or beat, the atria (A) contract prior to the ventricles (V) in accordance with a prescribed timing or synchronized relationship, hence the term "AV synchrony." These contractions are typically manifest or measured by sensing electrical signals or waves that are attendant with the depolarization of heart tissue, which depolarization immediately precedes (and for most purposes can be considered concurrent with) the contraction of the cardiac tissue. These signals or waves can be viewed on an electrocardiogram (ECG) and include a P-wave, representing the depolarization of the atria; the QRS-wave (sometimes referred to as a R-wave, the predominant wave of the group), representing the depolarization of the ventricles; and the T-wave, representing the repolarization of the ventricles. (It is noted that the atria also are repolarized, but this atrial repolarization occurs at approximately the same time as the depolarization of the ventricles; and any electrical signal generated by atrial repolarization is generally minute and masked out by the much larger QRS-wave on the ECG.)

Thus, it is the P-QRS-T cycle of waves that represent the natural AV synchrony of the heart. These waves, including the timing relationships that exist therebetween, are carefully studied and monitored through conventional ECG techniques whenever the operation and performance of the heart is being examined.

A pacemaker is a medical device that assists the heart in maintaining a desired AV synchrony by producing stimulation pulses that are directed to an appropriate chamber of the heart in order to cause that chamber to depolarize, and hence contract. (Because the main function of the pacemaker is to provide such stimulation pulses, it is frequently referred to as a "pulse generator.") That is, if for some reason the heart is unable to maintain its natural AV synchrony, a pacemaker is utilized to monitor the heart and to provide electrical stimulation pulses when it senses the heart is not maintaining a proper AV synchrony. A dual chamber pacemaker, for example, monitors both the right atrium and right ventricle. If it senses an atrial depolarization at appropriate times, no atrial stimulation pulse is generated. If it senses a ventricular depolarization within a prescribed time after the atrial depolarization, no ventricular stimulation pulse is generated. If however, it fails to sense either the atrial or ventricular depolarization within prescribed time periods, then stimulation pulses, frequently referred to as an A-pulse (if delivered to the atrium) and a V-pulse (if delivered to the ventricle), are generated and delivered to the appropriate chamber of the heart at an appropriate time in order to maintain the correct heart rhythm.

A premature ventricular contraction (PVC) is a premature ventricular depolarization that results from an ectopic beat originating from one of the ventricles. A PVC is thus a ventricular event that occurs out of sequence, i.e., after a previous ventricular event without a prior intervening atrial event (P-wave or atrial pacer pulse). Thus, e.g., the natural AV synchrony of the heart may be represented by the sequence

PRPRPRPRPR..., where "P" signifies an atrial event (which could be either an A-pulse or a naturally occurring P-wave) and "R" indicates a ventricular event (which event can either be a V-pulse, or a naturally occurring R-wave). In contrast, the occurrence of a PVC might be represented, e.g., by the sequence

PRRPRPRPRRPR..., where the two consecutive R's indicate two ventricular events without an intervening atrial event. (It should be noted that the PVC sequence shown above is only one of several possible sequences that may result from the occurrence of a PVC. Indeed, as explained below, the problem with a PVC is that it can trigger so many different responses from a pacemaker, some of which responses are highly undesirable as they prevent the heart from resuming its natural AV synchrony.) The present invention is directed to a system and method of assuring that when a true PVC does occur, i.e., two consecutive ventricular events without an intervening atrial event, a pacemaker response results, if needed, that leads the heart back to its normal AV synchrony.

The normal sequence of events in a cardiac cycle begins with a stimulation pulse provided by the sino-atrial (SA) node of the right atrium, which stimulation pulse causes the atria to contract, i.e., causes the P-wave. (For this reason, the SA node is frequently referred to as the heart's natural pacemaker, as it sets the pace or rate at which the heart naturally beats.) As has been indicated, the P-wave is the result of the atria (both left and right atrium chambers) depolarizing and thus producing atrial contraction. When a dual chamber pacemaker is employed, this P-wave is detected by the pacemaker's sense amplifier via an atrial lead located in the atrial chamber of the heart. The P-wave depolarization then conducts through the AV node of the heart into the ventricles. As it does so, it is naturally delayed an appropriate amount, typically between 100 and 200 milliseconds, to allow the blood (being pushed from the atria by the contraction of the atria) to fill the ventricles. As the depolarization stimulus travels towards the ventricles, ventricular depolarization occurs. The QRS-wave is the result of this depolarization and thus represents ventricular contraction (which contraction pushes the blood from the ventricles to other parts of the body). This ventricular depolarization is also detected by the pacemaker's sense amplifier via a ventricular lead located in the ventricular chamber of the heart. It is sensed as an R-wave. When sensed, the pacemaker resets its timing circuits and inhibits the next scheduled pacer pulse to the ventricles. This cycle of events repeats when the SA node, after a period of recovery from the last depolarization, starts another cycle of a P-wave followed by an R-wave, and so on. If, at any point in the cycle, a P-wave or R-wave is not sensed, then the pacemaker provides an appropriate stimulation pulse in order to maintain the synchrony of the heart.

Unfortunately, a PVC does not follow the abovedescribed normal cycle of events because a ventricular event, i.e., an R-wave, is premature, happening before the next atrial event, e.g., P-wave. It is thus important for the pacemaker to reliably detect a PVC and to distinguish this event as unique. Otherwise, the pacemaker would respond by, e.g., resetting the timing circuits of the pacemaker in a manner that precludes sensing of a subsequent P-wave or R-wave, which action could cause A-pulses or V-pulses to be generated at inappropriate times, all of which could significantly disrupt the AV synchrony of the heart. Many of these problems resulting from the occurrence of a PVC in a patient with a dual chamber pacemaker are described more fully in applicant's prior patent, U.S. Pat. No. 4,788,980, which patent is incorporated herein by reference.

Recognizing this problem, it is common in the art for programmable dual chamber pacemakers to change the timing of the next cardiac cycle following the sensing of a PVC, which changed timing might include the extension of the atrial refractory period. (The atrial refractory period, as explained more fully below, is that period of time subsequent to the generation of a stimulation pulse or the sensing of depolarization during which no cardiac events are sensed.) This is done to avoid sensing retrograde conduction. Retrograde conduction, as explained in the referenced patent, is a condition where the depolarization of the ventricles propagates backwards into the atria, causing the atria to depolarize, which atrial depolarization in turn propagates through the AV node into the ventricles, causing the ventricles to depolarize I f retrograde conduction originating from a PVC continues over several cardiac cycles, a tachycardia may result. (A tachycardia is a very rapid rhythm or rate of the heart.)

Where a pacemaker is employed, operating in either the DDD or VDD modes, common operating modes for a patient having an abnormal AV conduction path, the pacemaker itself may cause the tachycardia by tracking each P-wave caused by the retrograde conduction, and providing a ventricular stimulation pulse a programmed P-V delay thereafter. The pacemaker thus provides the forward conduction path (from the atria to the ventricles) electronically by tracking each P-wave and generating a V-pulse (ventricular stimulation pulse) if no R-wave is sensed within a prescribed time thereafter (the programmed P-V delay). The reverse or backward conduction path (from the ventricles to the atria) is provided by retrograde conduction originating with the depolarization of the ventricles, which depolarization occurs as a result of the V-pulse. Thus, retrograde conduction passes the ventricular depolarization back to the atria, causing the atria to depolarize (resulting in a retrograde P-wave), and the process repeats. This is known as a Pacer Mediated Tachycardia, or PMT. Unfortunately, the occurrence of a single PVC can reset the pacemaker timing in a manner that allows the pacemaker to begin tracking retrograde P-waves, causing a PMT to occur. Hence, it is critically important that the pacemaker reliably sense a PVC and take appropriate action to prevent a PMT from being triggered.

One response to a PVC known in the art is for the pacemaker to revert to a DVI mode of operation for one cycle. (For an explanation of the various pacemaker modes, DDD, DDI, DVI, VVI, etc., see, e.g., U.S. Pat. No. 4,712,555.) This response, in effect, turns off the atrial sense amplifiers for one cycle. Thus, subsequent to the detection of the PVC, no P-waves can be sensed by the pacemaker because the electronic sense circuits are masked from sensing any atrial events, whether a retrograde event or a normal event. Hence, it is not possible for the pacemaker to generate a V-pulse one P-V delay after a retrograde P-wave, because the retrograde P-wave is not sensed, thus preventing a PMT. One problem with this approach is that if during the one cycle DVI response a normal sinus rhythm with spontaneous R-wave occurs, the PVC response remains on because the pacemaker interprets the spontaneous R-wave as another PVC, there having been no intervening atrial event (at least not one that was sensed, because the atrial sense circuits were off). Thus, even though a possible PMT is prevented, the loss of normal P-wave tracking may occur because P-waves are masked by the PVC response, and any R-wave is thus interpreted as a PVC. Hence, the PVC response may become "stuck", as there is no way for it to terminate. Loss of P-wave tracking may occur from seconds to hours depending on the pacemaker's programmed rate settings and the patient's sinus rate (i.e., the P-wave rate set by the SA node).

Another PVC response known in the art is to extend the Post Ventricular Atrial Refractory Period (PVARP) by a prescribed amount, such as 480 msec, thus masking retrograde conduction during this period of time. (This PVC response is referred to hereafter as the "+PVARP on PVC response," or simply a "+PVARP response.") In addition, the atrial escape interval (VA delay) is fixed to a prescribed value, such as 830 msec, regardless of the programmed or sensor indicated rate (if a sensor is used, such as is the case in a rate-responsive pacemaker). See U.S. Pat. No. 4,788,980. The difference between the selected PVARP value and the fixed VA delay, which difference is 350 msec for the example given, allows a P-wave to be detected. This approach is an improvement over the DVI on PVC approach described above because the extended PVARP interval is sufficient to mask most retrograde conduction in the majority of patients, and P-waves not related to retrograde conduction can still be tracked. However, unless the sinus P-wave or other atrial event (e.g., an A-pulse) occurs during the time period subsequent to the extended PVARP interval and prior to the termination of the VA delay (e.g., during the 350 msec time period for the example times given above), the PVC response continues. This can occur if P-waves fall within the extended PVARP interval (which will not be detected) followed by R-waves that cause the VA delay interval to be reset (with the R-waves being interpreted as PVCs). This PVC response will have a fixed atrial escape interval and will slow the ventricular rate down because the rate of pacing is made up of the AV delay and the atrial escape interval (VA delay).

Further, with the new technology of activity sensors used for rate responsive pacing, the pacing rate is controlled by a separate sensor that detects patient activity (or some other parameter indicative of the need to adjust the heart rate). If such an activity sensor is employed, and if the +PVARP response remains stuck in the PVC response, then the patient may suffer from a lower ventricular rate controlled by the PVC response and not by the sensor indicated rate, which may be at a much higher rate than the PVC response controlled rate. For example, if the AV delay is 150 msec, then the rate during a +PVARP on PVC response would be, using the same numbers presented above, 150 msec +830 msec =980 msec, or about 61 beats per minute. Any intrinsic P-waves falling within the +PVARP interval are not sensed, hence the +PVARP response remains on when accompanied by detected R-waves prior to the end of the VA delay, and thus prevents sensor controlled rates from being effective since the +PVARP response controls the atrial escape interval. In other word, since the +PVARP response slows the ventricular rate down from a higher sensor controlled rate, it is more likely that a sinus will keep the +PVARP response on, thereby causing the slower ventricular rate, which rate may be undesirable when the patient needs increased cardiac output during activity. Thus, the +PVARP response to a PVC may not be appropriate for a sensor driven rate responsive pacer.

In order to avoid a falsely detected PVC, particularly in a rate-responsive pacer, it is known in the art to shorten PVARP with increased sensor or P-wave activity. Such approach allows better P-wave tracking before a P-wave falls into the PVARP interval (i.e., it enlarges the time interval during which a P-wave may be sensed, which time interval is the difference between PVARP and the VA delay). Of course, once a P-wave falls into the PVARP interval, it is not tracked. Such an approach also reduces the likelihood of a P-wave occurring during PVARP followed by an R-wave being interpreted as a PVC, again because it is more likely that the P-wave will not occur during the shortened PVARP interval. Nonetheless, even with this approach it is possible to remain in a PVC response once the response has been initiated because the events that need to be sensed to terminate the PVC response, e.g. a P-wave, are not sensed, as when they occur during the PVARP interval, or are not sensed for other reasons (such as due to lead dislodgment).

Another possible response to a PVC is to pace the atrium on the sensing of a PVC. This response, known as "A PACE ON PVC", is a selectable feature on the PARAGON pacemaker available from Pacesetter Systems, Inc., of Sylmar, California. However, at present this feature is not used because it has the potential of causing atrial competition. That is, since this response issues an atrial pulse with every sensed PVC, if atrial sensing has been lost (such as might occur, e.g., through lead dislodgment) every R-wave is considered as a "PVC" by the pacemaker PVC detection circuits.

What is needed, therefore, is a system for responding only to true PVC's, i.e., two sequential cardiac ventricular events without an intervening cardiac atrial event, and that minimizes the likelihood that a pacemaker will interpret a non-PVC as a PVC because the pacer fails to sense the intervening atrial event. Further, once a true PVC is detected, a response is needed that minimizes the likelihood of triggering a PMT, and that guides the heart back to its normal AV synchrony. Finally, a PVC response system is needed that assures the PVC response will terminate when appropriate, i.e., that the PVC response will not become stuck. The present invention advantageously addresses these and other needs.

SUMMARY OF THE INVENTION

In accordance with one aspect of the present invention, an implantable pacemaker, having means for detecting and responding to a premature ventricular contraction (PVC), includes circuit means for preventing the PVC detection means from providing a false PVC response. A "false PVC response," for purposes herein, is defined as a response to a sensed PVC that doesn't solve, or makes worse, the problems created by the occurrence of the events sensed as the PVC. Thus, interpreting certain events as a PVC, when in fact a true PVC has not occurred, and providing a certain pacemaker response as a result of this interpretation that is not needed (because no PVC really occurred) is one form of a false PVC response. One manner in which the present invention avoids false PVC responses is by maximizing the likelihood that a true PVC has occurred before any PVC response is triggered.

In accordance with another aspect of the invention, a pacemaker having PVC detection and response means further includes PVC response termination means for terminating a PVC response in the event the PVC response becomes stuck.

A preferred approach for maximizing the likelihood that a true PVC has occurred before a PVC response is initiated is to track P-waves that occur during the relative atrial refractory period of the pacemaker. Prior pacemakers have treated atrial events occurring during the relative atrial refractory period as noise. Thus, a P-wave occurring during this time is not recognized as a P-wave, and a subsequent R-wave is interpreted as a PVC (even though it is not a PVC, because it was preceded by a P-wave). The present invention also treats events occurring during the relative atrial refractory period as noise, but recognizes that such events could be a P-wave. Hence, a latch is set upon the occurrence of such atrial noise events. The setting of this latch prevents any subsequent R-wave from being interpreted as a PVC, i.e., the PVC detection circuitry of the pacemaker is disabled until the next ventricular event (R-wave or V-pulse) resets the latch.

Thus, in accordance with this preferred approach, the invention may be characterized as electronic circuit means for use in an implantable pacemaker for preventing the pacemaker from responding to a false PVC. The pacemaker in which the electronic circuit means is used includes at least means for sensing atrial and ventricular events, means for generating an atrial stimulation pulse, means for generating an atrial relative refractory time interval wherein sensed atrial activity is considered as atrial noise and not as a valid atrial event, and means for detecting a PVC and responding thereto in a prescribed manner. A PVC in such pacemaker is defined as two consecutive valid ventricular events without an intervening valid atrial event. The electronic circuit means for preventing the pacemaker from responding to a false PVC includes: (a) means for generating a latched signal in the event atrial noise is sensed during the atrial relative refractory time interval; and (b) means responsive to the latched signal for causing the PVC detecting means to assume a disabled state, this disabled state continuing until the first occurrence thereafter of a prescribed re-enabling event. The prescribed re-enabling event is preferably the occurrence of a ventricular event (i.e., an R-wave or a V-pulse).

With this circuit means, a PVC is not detectable by the PVC detecting means subsequent to the occurrence of atrial noise until the re-enabling event occurs. Hence, a ventricular event occurring subsequent to the occurrence of, e.g., an early atrial event (one that happens to fall into the atrial relative refractory time interval), which early atrial event is thus not considered by the pacemaker as a valid atrial event (even though it may be a valid atrial event, just an early one), is not detected by the PVC detecting means as a PVC because the occurrence of the early atrial event disables the PVC detection means. While such an approach opens up the possibility that atrial noise (e.g., not an early P-wave) may disable the PVC detecting means of the pacemaker and thus prevent a true PVC from being detected, it is felt that the consequences of failing to detect a true PVC when in fact one did occur are far less significant than detecting a false PVC and responding as though a PVC had occurred.

A preferred method for terminating a stuck PVC response in accordance with the present invention is to drop the nth beat of a PVC response cycle. This method thus allows any PVC response, such as the DVI on PVC response, or a +PVARP response, to last for only a programmed number (n) of cardiac cycles before the PVC response is automatically turned off. The value of n may be any integer value, but will typically be at least three and not more than ten. In one embodiment, n is set equal to four.

One characterization of this preferred method may thus be stated as a method for automatically terminating a stuck PVC response of an implantable pacemaker comprising: (a) enabling a PVC response mode of the pacemaker in response to the sensing of a PVC; (b) monitoring the number of cardiac cycles that occur while the PVC response mode is enabled; and (c) disabling the PVC response mode if the number of cardiac cycles occurring during the PVC response mode reaches n, where n is an integer greater than two. Advantageously, this method may readily be used with any of the previously described PVC response modes, such as DVI on PVC, +PVARP on PVC, A PACE ON PVC, or any other desired PVC response, thereby allowing the respective advantages of each PVC response mode to be realized, without concern that the response might become stuck for prolonged periods of time.

Further, the present invention contemplates that other sensing techniques may be used, either alone or in combination with each other (or in combination with other sensing techniques), for assuring that a true PVC has occurred prior to invoking a PVC response mode. Such sensing techniques may also be used to help determine if an appropriate response to the PVC is being made once the PVC has been detected. One sensing technique is to measure the pulse-signature (morphology) of the detected ventricular events. Because a normal QRS waveform has a shape and amplitude that is different from a PVC, the normal QRS pulse signature can be saved (and updated periodically, as required) and used as a reference to determine if a normal R-wave is being sensed as opposed to a PVC. This technique not only helps identify a true PVC, but also may be used once a PVC response has been initiated to verify that the PVC response should continue. If during a PVC response, for example, normal QRS pulse signatures are measured, then the PVC response is aborted.

Another sensing technique that may be used is to measure the retrograde conduction time, sometimes referred to as the R-wave to P-wave timing. In a normal pacemaker, this time is disguised by PVARP, and is not measured. However, in accordance with this invention, this time (i.e., the time between an R-wave and a P-wave occurring during PVARP) is measured. If over several cycles this time is stable, that provides some indication that retrograde conduction is present. In contrast, the lack of a stable interval may indicate sinus rhythm, thereby allowing a stuck PVC response to be safely aborted.

It is a feature of the present invention to provide a safe and reliable circuit that can be used within an implantable pacemaker that improves the ability of the pacemaker to distinguish true PVC's from other events that have heretofore been interpreted as PVC's, but were not.

A further feature of the invention is to provide such a circuit that prevents a PVC response of the pacemaker from becoming stuck. Such feature, in accordance with one embodiment of the invention, allows a PVC response of the pacemaker to continue for only a prescribed number of consecutive cardiac cycles. A related feature of the invention allows such prescribed number of consecutive cardiac cycles to be programmably selected, thereby allowing the pacemaker to be customized to suit the needs of a particular patient.

Yet another feature of the invention provides an PVC detecting and response means for use in an implantable pacemaker that provides a selectable PVC response only if certain events occur that are strongly indicative of a true PVC, and that provides no PVC response for events only suggestive of the possibility of a PVC. That is, the present invention is premised on a philosophy that the best PVC response may frequently be no response, i.e., no response different from the normal operation of the pacemaker, particularly where the occurrence of a PVC is questionable. Coupled with this philosophy is the premise that any PVC response that is provided should only continue for a short time, thereby avoiding situations where the PVC response might become stuck.

BRIEF DESCRIPTION OF THE DRAWINGS

The above and other aspects, advantages and features of the present invention will be more apparent from the following more particular description thereof, presented in conjunction with the following drawings, wherein:

FIG. is a typical ECG-type waveform illustrating the normal AV synchrony of the heart;

FIG. 2 is a block diagram of an implantable, programmable, dual-chamber pacemaker;

FIG. 6A is a timing diagram depicting a DVI on PVC response;

FIG. 9 is a timing diagram illustrating the operation of the PVC response termination portion of a preferred embodiment of the present invention, namely a circuit that terminates a PVC response after four cardiac cycles;

FIGS 10A-10C are, in combination, a logic schematic diagram of a preferred manner of implementing the present invention;

FIG. 11 is a table that defines the various options available when using the circuit of FIGS. 10A-10C by selectively setting the first four control bits of the PVC Control Register of FIG. 10C;

FIGS. 12A-12D are timing diagrams that illustrate the operation of the invention shown in FIGS. 10A-10C for various conditions;

FIG. 13 is a functional block diagram depicting an alternative embodiment of the present invention that recognizes true PVC's by monitoring the morphology of the R-wave and/or measuring/monitoring selected time intervals associated with atrial and/or ventricular events.

DETAILED DESCRIPTION OF THE INVENTION

Figure 3A:
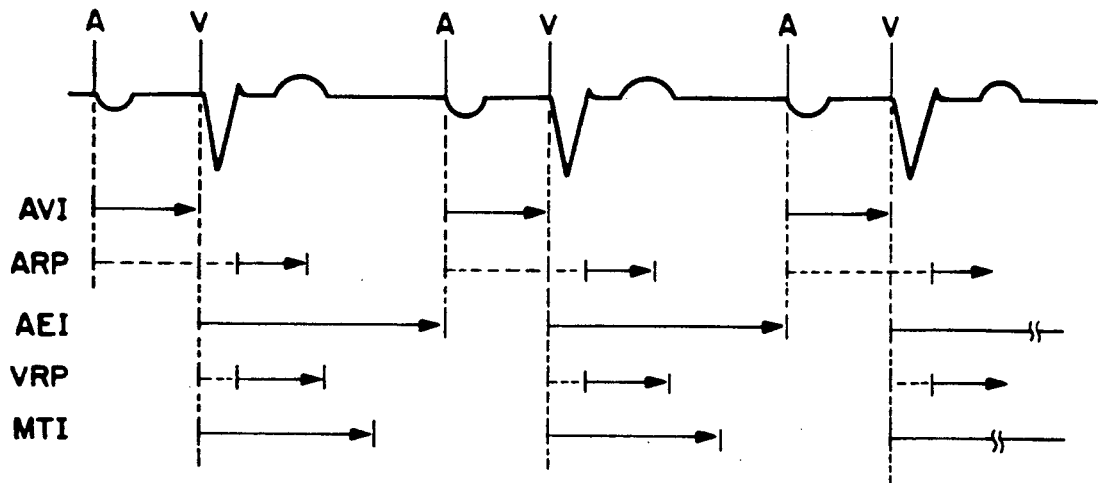
FIG. 3A is a composite timing diagram illustrating how the AV synchrony of the heart is maintained when both atrial and ventricular stimulation pulses are provided to the heart by a dual-chamber pacemaker.

The following description is of the best mode presently contemplated of practicing the invention. This description is not to be taken in a limiting sense, but is made merely for the purpose of describing the general principles of the invention. The scope of the invention should be ascertained with reference to the claims.

Referring to FIG. 1, there is shown a typical ECG-type waveform illustrating the normal operation and cardiac cycle of a heart. Such waveforms may be obtained using conventional skin electrode ECG techniques. Alternatively, intercardiac ECG features of modern pacemakers may provide similar ECG information through the use of the telemetry features of such pacemakers. Beginning at the left of the waveform there is shown a P-wave. This P-wave represents the electrical activity coincident with the depolarization of the atria of the heart. Depolarization of the atria is accompanied by contraction of the atria, thereby allowing blood to be pushed from the atria into the ventricles of the heart. While those skilled in the art will recognize that depolarization and contraction are not necessarily simultaneous events, they will be assumed to be simultaneous events for purposes of this patent application, and the terms "depolarization" and/or "contraction" are meant to be synonymous.

A short time subsequent to the generation of the P-wave, the QRS complex appears, representing the depolarization of the ventricles. The time period between the P-wave and the QRS wave (often referred to as simply an R-wave) is a very important time interval in the operation of the heart because it represents the time needed for the blood to flow from the atria into the ventricles. The R-wave is followed by a T-wave, which wave represents the electrical activity associated with the repolarization of the ventricles. As known to those skilled in the art, the ventricles do most of the work in pumping the blood throughout the body. Typically, one heart beat or heart cycle is measured as the time interval between succeeding R-waves, simply because the R-wave typically represents the easiest of the waves to identify and measure. A heart beat could, of course, be measured relative to any point within the heart cycle, such as between succeeding T-waves or P-waves.

The important point to recognize is that a certain rhythm or synchrony must occur if the heart is to function efficiently. That is, the depolarization of the atria, represented by the P-wave, must be followed a short time thereafter by the depolarization of the ventricles, represented by the R-wave. After a sufficient delay, the atria must again depolarize, followed by the depolarization of the ventricles. If the depolarization of the atria or ventricles do not occur naturally, then a pacemaker may be employed to provide stimulation pulses to these respective heart chambers, in order to trigger the required depolarization/contraction at the appropriate time periods of the heart cycle.

Referring next to FIG. 2, a block diagram of a typical atrial tracking dual-chamber pacemaker 10 is illustrated. Pulse Generator and Control Logic 12 generates the appropriate timing sequences and stimulation pulses for delivery to the heart. Stimulation pulses are delivered to the right atrium of a heart (not shown) through an atrial drive amplifier 14 and an atrial lead or conductor 16. This same atrial lead 16 is connected to an atrial sense amplifier 18. This sense amplifier 18 monitors the electrical activity of the atrium to determine if a sinus P-wave, representing the natural depolarization of the atrium, has occurred. If such sinus atrial activity is sensed, then the Pulse Generator 12 inhibits the stimulation pulse provided to the drive amplifier 14 and provides for a ventricular stimulus after a predetermined time period (referred to as the sensed AV delay). However, if after a prescribed period of time, typically referred to as the atrial escape interval, a sinus P-wave has not been sensed, then the Pulse Generator 12 delivers a stimulation pulse, through the drive amplifier 14, to the atrium over lead 16. The pulse width and amplitude of this stimulation pulse are controlled by the Pulse Generator and Control Logic 12.

In a similar manner, the Pulse Generator and Control Logic 12 senses the electrical activity occurring in the right ventricle of the heart through a sense amplifier 20 connected to a ventricular lead 22. If naturally occurring ventricular electrical activity is not sensed within an appropriate ventricular escape interval, then the Pulse Generator and Control Logic 12 generates a ventricular stimulation pulse of a prescribed pulse width and amplitude, delivered through the drive amplifier 24, in order to cause the desired ventricular contraction.

Clock circuitry 26 provides the basic clock signals from which the pulse generator and control logic 12 operates. Telemetry and communications circuitry provides a means whereby information can be telemetered to and from the implanted pacemaker. Control information that varies the basic escape intervals of the pacemaker, for example, may be received through the telemetry and communications circuitry 28 and stored in a memory 30, as may control information that sets the desired pulse width and/or amplitude of the stimulating pulse. Such control information may also be passed directly to the Pulse Generator and Control Logic 12, if desired. Similarly, electrical activity of the heart, as sensed through the sense amplifiers 18 and 20, can be telemetered external to the pacemaker through the telemetry and communications circuitry 28, thereby allowing an attending physician or other medical personnel, e.g., cardiologist, to monitor the activity of the heart without the use of external skin electrodes. A magnetic reed switch 32 is also typically employed with implanted pacemakers in order to control the programmable functions of the device. With a suitable programming apparatus in place, the attending physician or cardiologist can effectuate any desired changes in the operation of the pacemaker by sending appropriate control signals and commands over the telemetry and communications circuitry 28.

Referring next to FIG. 3A, a composite timing diagram illustrating the operation of a typical demand-type, dual-chamber pacemaker, is illustrated. In this and other timing diagrams used herein, the stimulation pulses generated by the pacemaker are illustrated as a narrow spike labeled with either an A (for an atrial stimulation pulse) or a V (for a ventricular stimulation pulse). Further, the response of the heart to an applied stimulation pulse is indicated in the figures as having an opposite polarity from that shown in FIG. 1. (FIG. 1 depicts the natural or sinus rhythm of the heart, and thus the heart responds without the application of a stimulation pulse.) This is done to clearly distinguish in the figures naturally occurring events of the heart from pacer-induced (paced) events.

Included in the timing diagram of FIG. 3A are representations of the various timing intervals that are generated by the control logic 12 (FIG. 2). Many of these time intervals are programmable, meaning that the length of such intervals can be varied by sending appropriate control signals over the telemetry and communications circuitry 28 to the memory circuits 30 of FIG. 2. As known to those skilled in the electronic arts, there are numerous methods and techniques through which a time interval can be varied. One such technique involves loading an appropriate data word into a prescribed memory location, which data word can in turn be subsequently loaded into an appropriate counter of the control logic 12. A basic clock signal may then be used to clock this counter until the desired count is reached, at which time a terminal count signal (frequently termed a "timed out" signal) is generated to indicate the end of the desired time interval. By merely changing the value of the data word that is loaded into memory, the length of the time interval can thus be varied or programmed to a desired value.

The time intervals shown in the timing diagrams that follow are indicated by a horizontal line. If the time interval has "timed out" —that is, if it has reached its terminal count—an arrowhead is placed on the horizontal line, pointing to the point in time at which the time interval terminates. (The horizontal axis of the timing diagrams represents the time axis.) It is noted that the timing drawings are not necessarily drawn to scale, nor with linear horizontal or vertical axes. It is also noted that some cardiac events, such as the T-wave, are omitted from some of the timing diagrams. If a sensed electrical event occurs prior to the termination of a given interval, which event inhibits the generation of a stimulation pulse (or alters some other operation of the pacemaker) then a dot is placed on the horizontal line indicating the point in time at which the sensed event terminates or resets that particular interval.

Shown in FIG. 3A are five basic time intervals. These are: (1) the AV interval, or AVI, representing the desired time interval between atrial depolarization and ventricular depolarization; (2) the atrial refractory period, or ARP, representing the time interval subsequent to the generation of an atrial stimulation pulse or sensed atrial event during which the atrial sensing circuits may be disabled; (3) the atrial escape interval, or AEI, representing the time interval after which, in the absence of naturally occurring atrial activity during such interval, an A-pulse is generated and delivered to the atrium (sometimes also referred to as the VA interval); (4) the ventricular refractory period, or VRP, representing the interval during which the ventricular sense amplifier 20 (FIG. 2) is disabled; and (5) the maximum tracking interval, or MTI, representing the interval where P-waves will be tracked up to the maximum tracking rate. (The MTI+AVI thus define the shortest possible time period of a cardiac cycle, and hence, the maximum possible paced ventricular rate.)

Figure 3B:
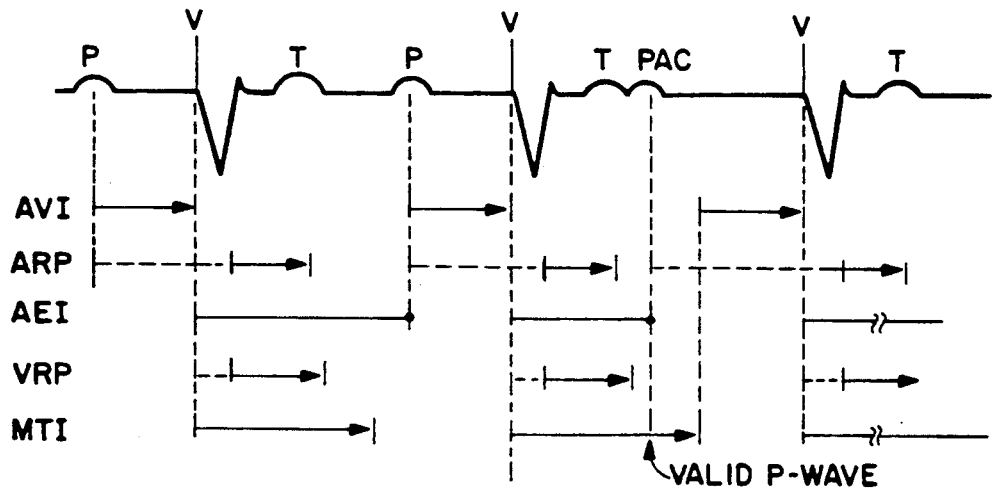
FIG. 3B is a similar composite timing diagram illustrating how AV synchrony is maintained when only a ventricular stimulation pulse need be provided to the heart, and further illustrates one possible response of a pacemaker to a premature atrial contraction (PAC)
Figure 3C:
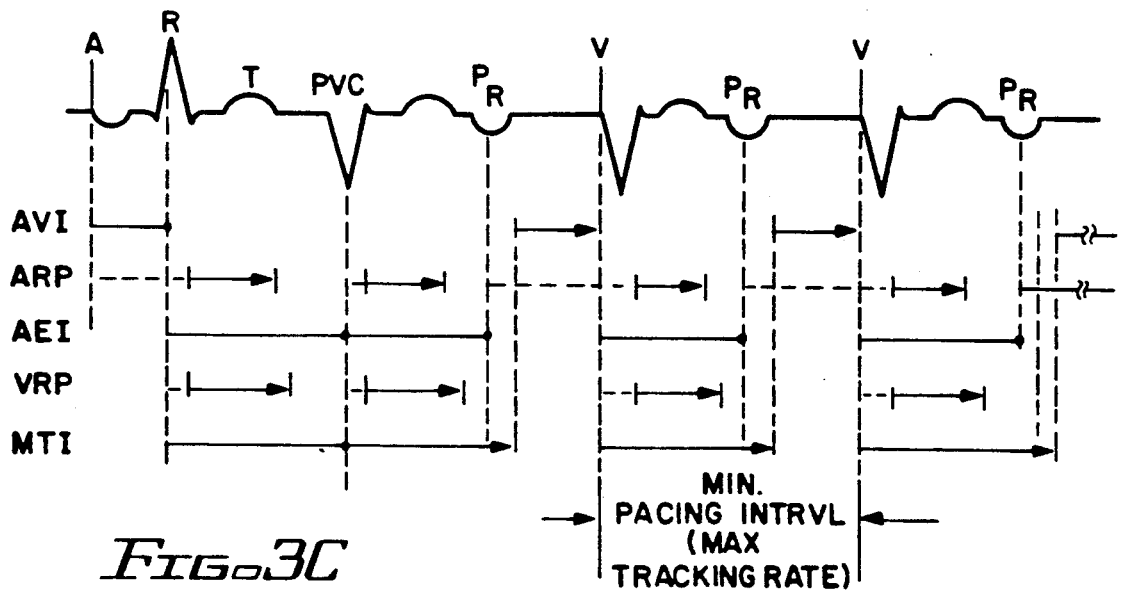
FIG. 3C is a similar timing diagram illustrating one possible way in which a PMT may be triggered.

With the above timing intervals thus defined, the following description of FIGS. 3A-3C can be better understood. As indicated previously, FIG. 3A illustrates how a pacemaker is used to maintain a desired rhythm or synchrony of the heart. For the situation shown in FIG. 3A, it is assumed that the heart being stimulated cannot provide its own atrial or ventricular contractions at a suitable rate, and that the pacemaker must therefore provide the stimulation pulses required to maintain the desired heart rate. Accordingly, an atrial stimulation pulse "A" is provided in order to invoke a contraction of the atrium. This event triggers both the A-V interval, AVI, and the atrial refractory period, ARP. A portion of the ARP, designated in the figures as a dashed line, is an absolute refractory period, meaning that the atrial sense amplifier 18 (FIG. 2) is totally blanked or inoperable. A subsequent portion of the ARP, represented in the figures as a solid line, may include both absolute (e.g., the first 100 milliseconds) and relative (e.g., the remainder of the period) refractory periods. Any signals sensed during the relative refractory period are considered as noise. At the termination of the AVI, a ventricular stimulation pulse, V, is generated and applied to the heart. This stimulation pulse causes the ventricle to contract, as indicated by the inverted R-wave. The generation of the ventricular stimulation pulse, or V-pulse, also triggers the beginning of the atrial escape interval, or AEI; the ventricular refractory period, or VRP; and the maximum tracking interval, or MTI. At the conclusion of the AEI (or V-A interval), there having been no P-waves sensed, an A-pulse is generated in order to produce a contraction of the atrium, thereby initiating the next cycle of the heart. Thus, the events previously described begin again and the cycle repeats itself, with a V-pulse being generated after the AVI subsequent to the A-pulse, and an A-pulse being generated after the AEI subsequent to the V-pulse. In this manner, the desired rhythm of the heart is maintained.

In FIG. 3B, it is seen that a natural or sinus P-wave is present, and hence there is no need for the pacemaker to generate an A-pulse. When the sinus P-wave is sensed, the AVI is initiated, and the pacemaker is alert in order to sense if an R-wave will occur. If an R-wave has not been sensed by the time the AVI times out, then a V-pulse is generated as indicated. This V-pulse initiates the beginning of the atrial escape interval. Prior to the termination of the AEI, a naturally-occurring P-wave is sensed, indicated by the dot on the AEI line. The sensing of the naturally-occurring P-wave inhibits the generation of an A-pulse, and initiates the beginning of a new AVI, at the conclusion of which another V-pulse is generated. This process continues for so long as the heart continues to generate sinus P-waves but fails to produce naturally-occurring R-waves.

FIG. 3B further illustrates one possible response of the pacemaker to a premature atrial contraction, or PAC. A premature atrial contraction is simply a contraction of the atrium that occurs prematurely or early in the normal AV synchrony. The PAC shown in FIG. 3B occurs immediately subsequent to the second T-wave. The pacemaker responds to the PAC as though it were a sinus P-wave. That is, the occurrence of the PAC terminates the atrial escape interval. Further, when a P-wave occurs within the MTI, as does the PAC shown in FIG. 3B, a latch circuit is set indicating that the sensed activity is considered a valid P-wave. The setting of this latch causes the A-V interval to be initiated at the end of the MTI. At the conclusion of this A-V interval, the V-pulse is generated. Once a V-pulse has been generated, the operation of the pacemaker continues in normal fashion.

Referring next to FIG. 3C, a timing diagram is illustrated indicating one way in which a pacer mediated tachycardia, or PMT, may be generated. At the beginning of the sequence shown in FIG. 3C, it is assumed that an A-pulse is provided to stimulate a desired atrial contraction. A short time thereafter, subsequent to the termination of the A-V interval, a naturally occurring R-Wave is sensed. Hence, no V-pulse is generated, and the atrial escape interval and other intervals are initiated in normal fashion. However, a short time after the sensing of the R-wave, a premature ventricular contraction, or PVC, occurs. For purposes of illustration, it is assumed in FIG. 3C that the pacemaker cannot distinguish between the occurrence of an R-wave and a PVC. That is, the pacemaker simply senses that electrical activity has occurred in the ventricle, and it therefore assumes that such activity represents a normal ventricular contraction. Of course, as explained previously, a PVC does represent a ventricular contraction; however, it is a ventricular contraction out of sequence, that is, one that occurs subsequent to a preceding ventricle contraction but prior to the next atrial contraction, or (in the case of multiple sequential PVC's) prior to another PVC. As also explained previously, the occurrence of a PVC may, under the right circumstances, through retrograde conduction, cause the atrium to contract. Such a contraction is illustrated in FIG. 3C as a retrograde P-wave, labeled $P_R$. Hence, once the PVC occurs, followed by the retrograde P-wave, $P_R$, a V-pulse is generated a prescribed time thereafter. This prescribed time is at the conclusion of the maximum tracking interval, MTI, plus the A-V interval, AVI. In response to the V-pulse, the ventricle contracts. This contraction, through retrograde conduction, again causes a retrograde P-wave occur. This retrograde P-wave, $P_R$ is again followed by a V-pulse that occurs as soon as possible thereafter, which time is again set by the MTI+AVI intervals. Thus, in this sequence, the heart is paced at the maximum tracking rate, and a PMT is created. The PMT cycle is sustained by the retrograde path through which the retrograde P-wave occurs in response to a ventricular contraction and the anterograde path, provided by the pacemaker, through which a V-pulse is generated at the conclusion of MTI+AVI intervals.

Figure 4:
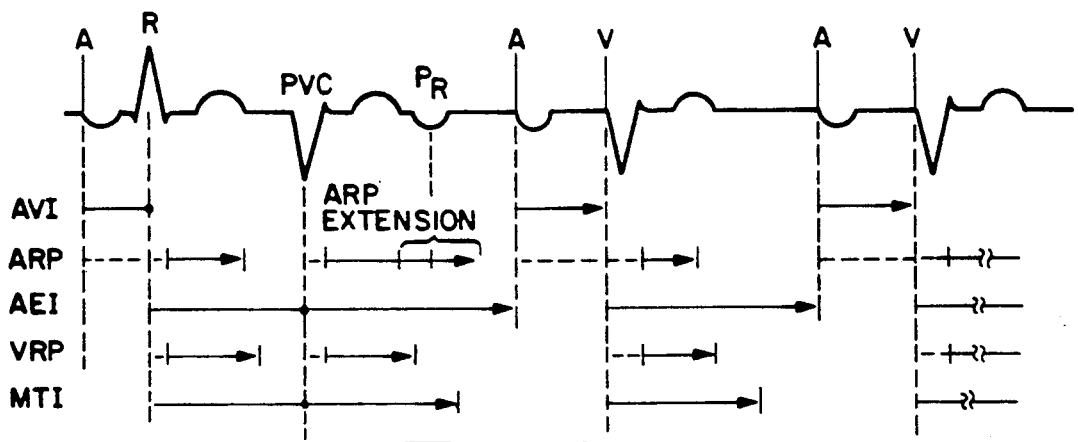
FIG. 4 is a similar timing diagram illustrating how extending the atrial refractory period may preclude the triggering of the PMT shown in FIG. 3C.

Referring next to FIG. 4, there is shown the prior art approach to the solution of the problem illustrated in FIG. 3C. In accordance with the teachings of the prior art, and as mentioned previously, logic circuitry can be employed to recognize the occurrence of a PVC. Once the occurrence of a PVC has thus been identified, then the control logic of the pacemaker extends the atrial refractory period for a prescribed amount. This extension is identified in FIG. 4 as the ARP EXTENSION portion of the atrial refractory period following the occurrence of the PVC. Advantageously, the ARP EXTENSION prevents the retrograde P-wave following the PVC from being sensed by the pacemaker. Accordingly, at the conclusion of the atrial escape interval, an A-pulse will be generated by the pacemaker. Following the A-pulse, a V-pulse will be generated one A-V interval thereafter, unless a natural R-wave occurs prior to the termination of the AV interval. Hence, the effect of the extension of the atrial refractory period as illustrated in FIG. 4 is that the atrium contracts twice, once in response to the PVC (through retrograde conduction), and once as a result of the applied A-pulse. Such double contraction of the atrium is, according to the teaching of the prior art, of little consequence so long as it only occurs in one cycle. Further, if the triggering of a PMT can be avoided, the benefits derived therefrom are felt to far outweigh the slight disruption of the AV synchrony that occurs in the one cycle in which the double atrial contraction occurs.

Figure 5:
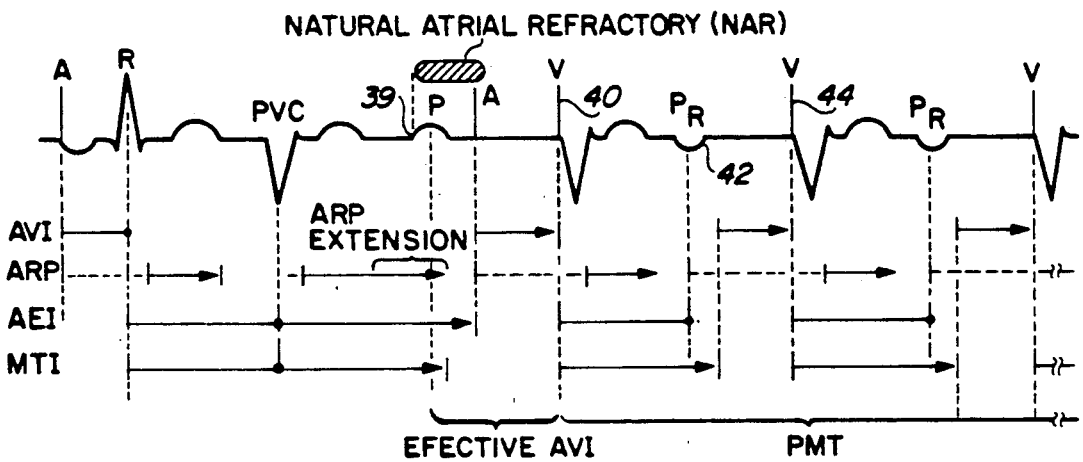
FIG. 5 is a composite timing diagram showing how extending the atrial refractory period, as was done in FIG. 4, may still cause a PMT to be triggered.

Unfortunately, as indicated in the timing diagram of FIG. 5, extending the atrial refractory period can itself create the conditions necessary to trigger a PMT. In FIG. 5, the atrial refractory period has been extended as in FIG. 4. A sinus P-wave occurs during this extended refractory period, but is not sensed by the pacemaker because the sense amplifier of the pacemaker is not operable during this time period. Also shown in FIG. 5, at the upper portion thereof, is a shaded time interval NAR. This is the time period during which the atrial muscle tissue is recovering from a depolarization/contraction, and therefore represents a time during which the atrium is physically incapable of contracting again. This natural atrial refractory period begins as the atrium begins to depolarize. It lasts until the atrial tissue is repolarized, which typically could be 150-300 milliseconds subsequent to the depolarization of the tissue. If, as shown in FIG. 5, the A-pulse is applied to the atrium at the conclusion of the atrial escape interval, as was done in FIG. 4, but also at a time that falls within the natural atrail refractory period, then this A-pulse will be ineffective. The net result of this ineffective action, in addition to representing a needless expenditure of energy from the pacemaker's battery, is that the A-V interval, AVI, as seen by the heart tissue, will be effectively extended or lengthened. This is also illustrated in FIG. 5 as the interval between the sinus P-wave 39 and the subsequently applied V-pulse 40. Lengthening the A-V interval generally enhances the likelihood that retrograde conduction will occur. FIG. 5 depicts the occurrence of such a retrograde P-wave 42 that occurs in application of V-pulse 40. A V-pulse 44 will then be applied as soon as permitted after retrograde P-wave 42, or at the maximum tacking rate. As this process repeats itself, a pacer mediated tachycardia, or PMT, is again present.

Referring next to FIG. 6A, a timing diagram depicting a DVI on PVC response is shown. As indicated above, such a response is known in the art for responding to a PVC. Advantageously, initiating a DVI response for one cycle prevents the sensing of any P-waves by the pacemaker sensing circuits. Hence, as shown in FIG. 6A, a retrograde P-wave 60, or any other P-waves, are not tracked, thus disallowing a ventricular pulse one AV delay later, thereby preventing a PMT. Rather, at the end of the atrial escape interval, AEI, an A-pulse 62 will be generated, which A-pulse resets the timing of the pacemaker and terminates the DVI response.

Figure 6B:
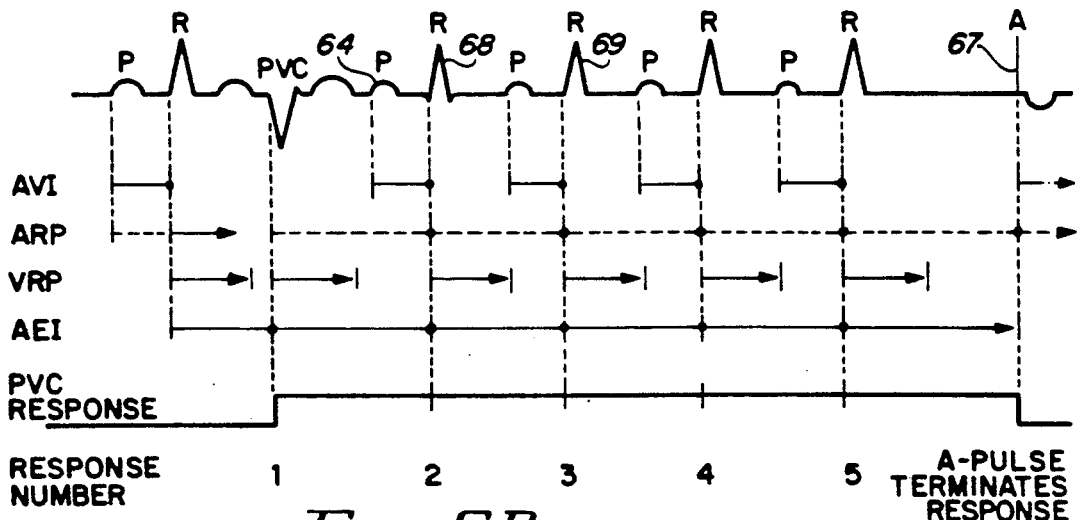
FIG. 6B is a timing diagram as in FIG. 6A illustrating how a DVI on PVC response may provide an inappropriate response.

Disadvantageously, as shown in FIG. 6B, if for any reason during the PVC DVI response, normal sinus rhythm occurs, manifest by, e.g., P-wave 64, followed by spontaneous R-waves, e.g., R-wave 68, the PVC response remains on because there is no A-pulse to signal its termination. Hence, R-wave 68 is interpreted as a PVC, as is the next R-wave 69, as are all the other R-waves that occur thereafter as a result of normal sinus rhythm. Each "detected PVC" maintains the pacemaker in its DVI mode for one more cycle, thereby preventing the P-waves from being sensed. Even through a true PVC has not occurred, the pacemaker logic interprets the sensed events as a PVC (a "false PVC"), and responds accordingly. Unfortunately, the situation depicted in FIG. 6B (of not tracking P waves, and hence interpreting sensed R-waves as a PVC) may last from seconds to hours, depending upon the pacemaker's particular programmed values and the sinus rate (P-wave rate) of the patient. For the situation shown in FIG. 6B, the PVC response lasts for five cardiac cycles, this response not being terminated until A-pulse 67 is generated.

In order to prevent the problem depicted in FIG. 6B (of continually interpreting sensed R-waves as a PVC because the preceding P-waves are not sensed due to the invoked DVI mode), the present invention advantageously includes a provision for automatically terminating the PVC response mode after a prescribed number of cycles. This termination feature is explained more fully below in conjunction with FIG. 9.

Figure 7:
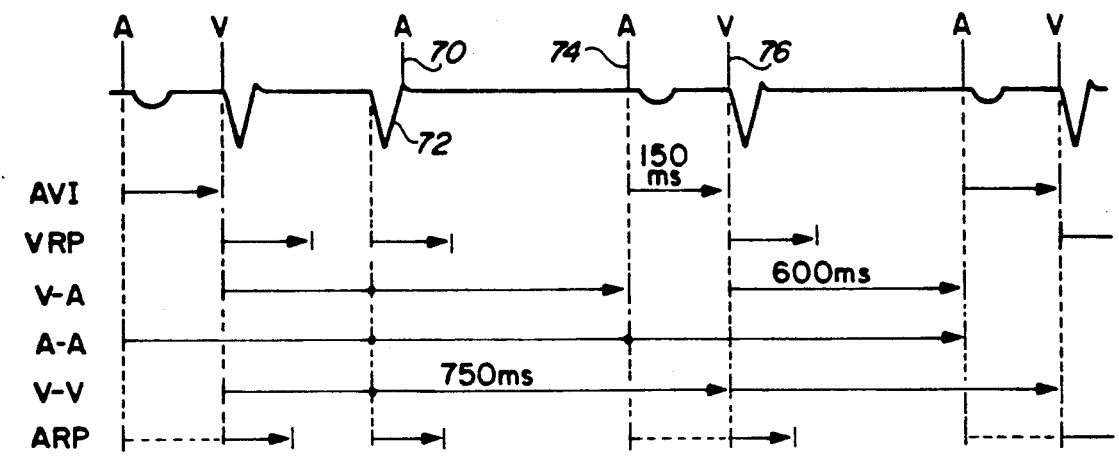
FIG. 7 is a timing diagram depicting A PACE ON PVC response.

FIG. 7 shows a timing diagram depicting the prior art technique of responding to a PVC known as "A PACE ON PVC". (In the timing diagrams that follow, FIGS. 7, 8, 9, and 12A-12D, note that the T-wave has been omitted from the ECG signals.) In accordance with this approach an A-pulse is issued with every sensed PVC. Thus, in FIG. 7, the occurrence of PVC 72 causes an A-pulse 70 to be issued. For the situation shown in FIG. 7, the issuance of the single A-pulse 70 is an appropriate response to the PVC that prevents further PVC's from occurring. This is because no intrinsic atrial activity is present. That is, the A-pulse 70 resets the timing of the pacer, thereby causing a second A-pulse 74 to be issued at the conclusion of the V-A delay, and a V-pulse 76 to be issued at the conclusion of the V—V delay (which is one AVI after the conclusion of the V-A delay). However, should intrinsic atrial activity be present, there is some likelihood that such activity (P-waves) will occur during the atrial refractory period subsequent to the A-pulse 70, and therefore not be sensed. Hence, any R-wave thereafter would be interpreted as a PVC, causing another A-pulse to be delivered. Also, a complete loss of sensing P-waves may occur due to lead dislodgment. In either event, such A-pulses may compete with any unsensed intrinsic atrial activity, causing irregular and inefficient operation of the heart. Because of this potential for atrial competition, A PACE ON PVC response has heretofore been generally disfavored. However, in accordance with the present invention, as explained more fully below, such A PACE ON PVC response may be used in (appropriate circumstances, as desired, because such response will not continue for more than a few cardiac cycles.

Figure 8:
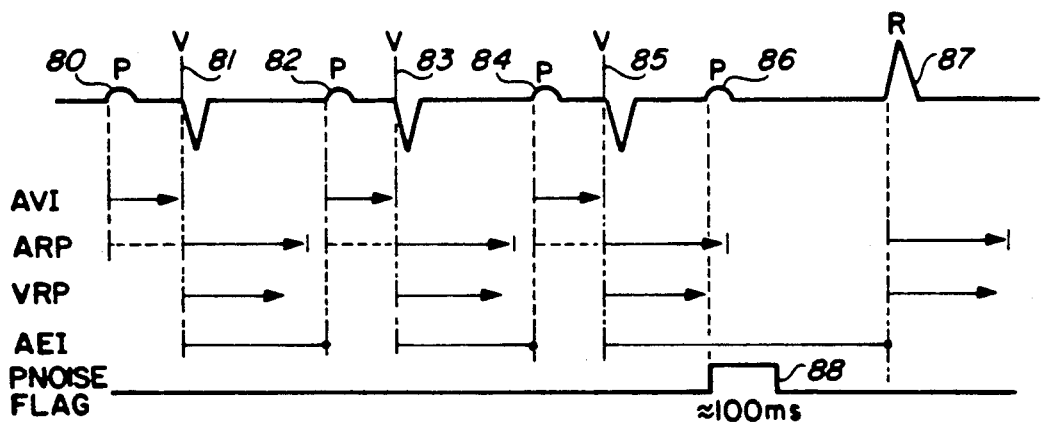
FIG. 8 is a timing diagram illustrating the operation of the preventative portion of a preferred embodiment of the present invention, namely, a circuit that disables the PVC detection means of a pacemaker in response to sensed atrial events occurring during the relative portion of the atrial refractory interval.

Referring next to FIG. 8, a timing diagram illustrating the operation of the preventative portion of a preferred embodiment of the present invention is illustrated. In accordance with this embodiment, a circuit is provided, detailed more fully below in connection with the description of FIGS. 10A-10C, that disables the PVC detection means of a pacemaker in response to sensed atrial events occurring during the relative portion of the atrial refractory period (ARP). For the situation shown in FIG. 8, the pacemaker is operating in an atrial tracking mode, i.e., providing V-pulses to stimulate the ventricle at the conclusion of the A-V interval (AVI) following detection of a P-wave if an R-wave is not detected during the A-V interval. That is, the pacemaker provides V-pulses on demand that follow atrial activity by the prescribed A-V interval. Hence, if an R-wave is detected prior to the termination of the A-V interval, the V-pulse is inhibited. However, for the situation shown during the first three cardiac cycles of FIG. 8, it is assumed that no such R-waves have occurred.

Thus, for the first three cardiac cycles shown in FIG. 8, i.e., for P-wave 80, followed by V-pulse 81 (first cycle), P-wave 82, followed by V-pulse 83 (second cycle), and P-wave 84, followed by V-pulse 85 (third cycle), the pacemaker operates in the atrial tracking mode as described above, providing stimulation pulses to the ventricle on demand. However, at the beginning of the fourth cardiac cycle, a P-wave 86 occurs prior to the termination of the atrial refractory period (ARP). In a conventional pacemaker, the P-wave 86 is thus treated as noise, and is not detected. Hence, a subsequent R-wave 87 would be interpreted as a PVC (when, in fact, it is not a PVC). To avoid this possibility, the circuit of the present invention detects P-waves during the atrial refractory period (ARP). Any P-waves sensed during the ARP are still treated as noise (i.e., their occurrence does not reset the pacemaker's timing circuits as would a sensed P-wave), but their occurrence sets a P-Noise flag, shown as pulse 88 in FIG. 8. The setting of the P-Noise flag 88 disables (turns OFF) the PVC detection capability of the pacemaker until an enabling event occurs to reenable (turn ON) the PVC detection capability. The enabling event is the next ventricular event (V-pulse or R-wave). Thus, in FIG. 8, the P-Noise flag 88 turns OFF the PVC detection capability of the pacemaker, thereby preventing the R-wave 87 from being interpreted as a PVC.

Turning next to FIG. 9, a timing diagram illustrating the operation of the PVC response termination portion of one embodiment of the present invention is shown. This embodiment terminates a desired PVC response after a programmed number of cardiac cycles. In FIG. 9, the occurrence of a PVC 90 triggers a +PVARP on PVC response, meaning that the atrial refractory period, ARP, is extended. For the situation shown in FIG. 9, this extension is 480 milliseconds (ms). A first extension 93a of the ARP prevents the next P-wave 91 from being detected by the pacemaker detection circuits as a valid atrial event. Hence, the next R-wave 92 is considered as a PVC, causing a second extension 93b of the ARP. This second extension likewise prevents the next P-wave 94 from being detected, resulting in the next R-wave 96 as also being interpreted as a PVC. The interpretation of R-wave 96 as a PVC again causes a third extension 93c of the ARP, preventing the next P-wave 98 from being detected. However, for the situation shown in FIG. 9, and in accordance with the present invention, the occurrence of R-wave 99 terminates the +PVARP on PVC response of the pacemaker. R-wave 99 represents the fourth "PVC" since the initial PVC 90 (including PVC 90 and R-waves 92, 96 and 99), and the termination circuit of the present invention is programmed, in accordance with the approach shown in FIG. 9, to terminate any PVC response after four such events. It is to be emphasized, of course, that the number four is only exemplary, as any desired number of cycles could be selected before the PVC response is automatically terminated.

Figure 10A:
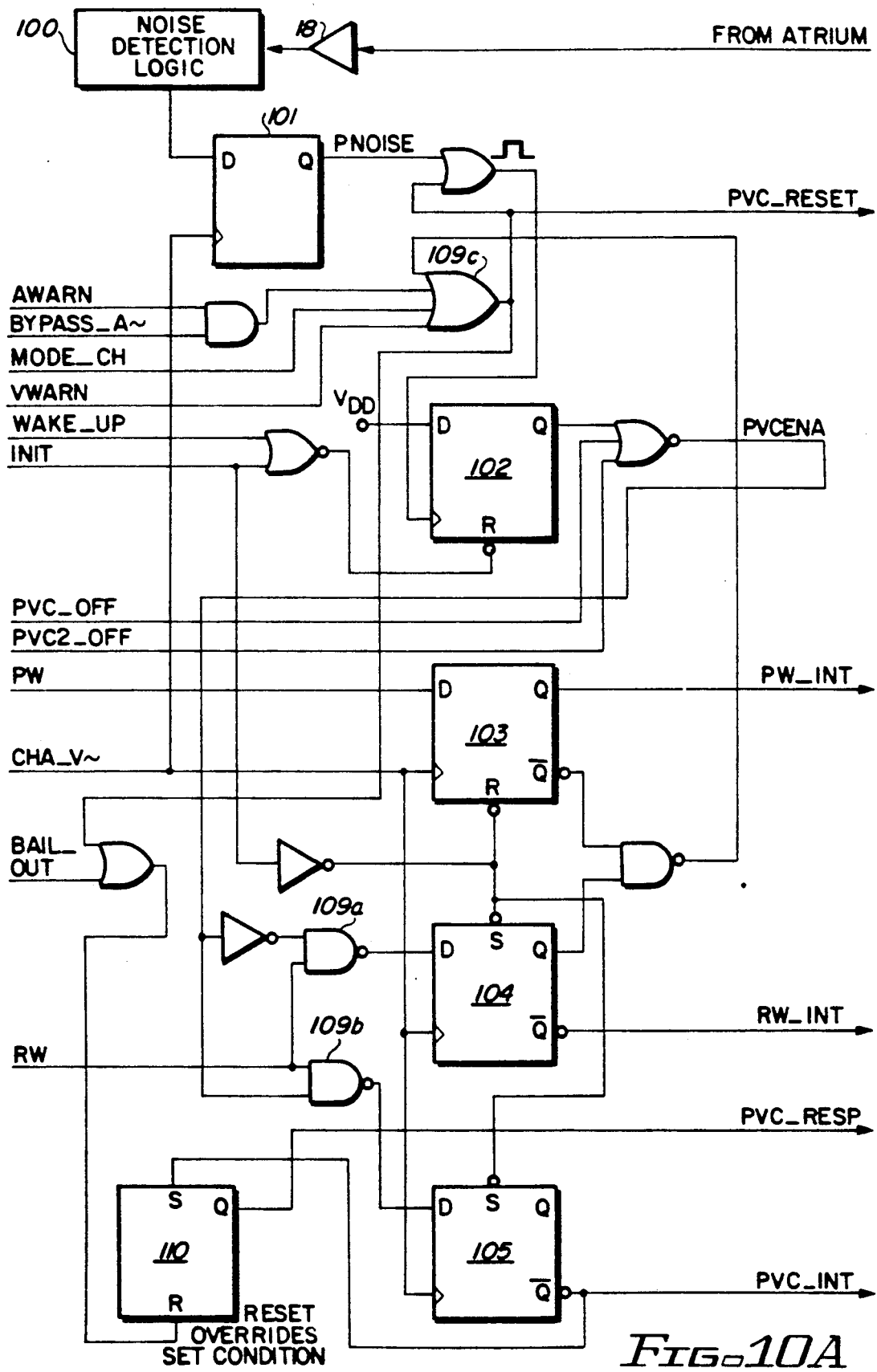
Figure 10C:
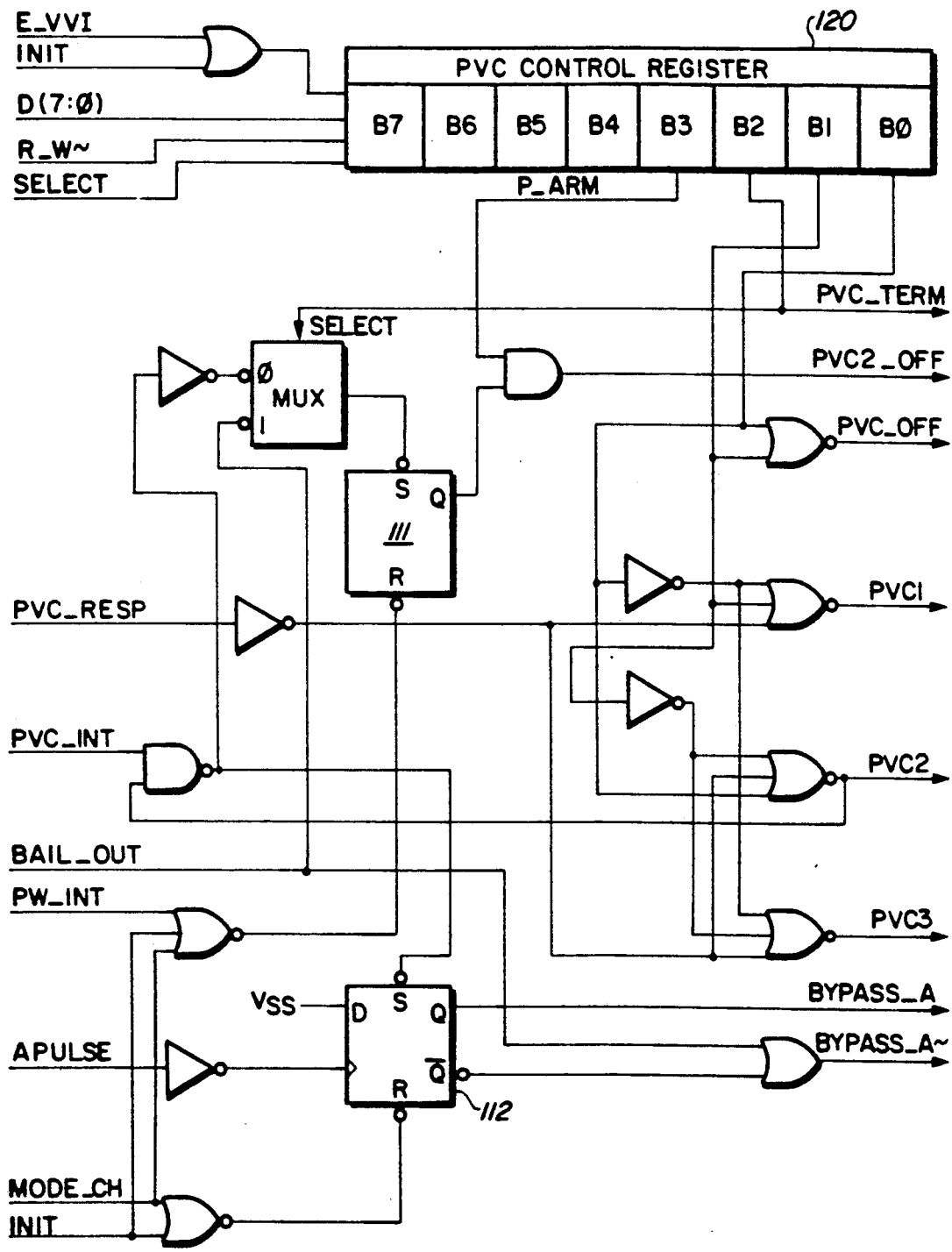

With reference next to FIGS. 10A-10C, a logic schematic diagram of a preferred manner of implementing the preventative and termination portions of the present invention is illustrated. The circuit shown in FIGS. 10A-10C may form part of the control logic 12 (FIG. 2) of the pacemaker with which the invention is used. Reference may be made to, e.g., U.S. Pat. Nos. 4,712,555 and 4,788,980 for exemplary teachings related to other details of the control logic of a multi-mode implantable pacemaker. As seen in FIGS. 10A-10C, the circuit includes, in combination, flip-flop circuits 101-108, 112, latch circuits various logic gates as shown, and a PVC control register 120. The signal names shown in FIGS. 10A-10C have the following meanings:

PNOISE: A signal indicating that atrial channel noise is present.
APULSE: A signal indicating an atrial pacer pulse (digital logic level) is present that is used to pace the atrium chamber of the heart. (Note, as used elsewhere in this application, an A-Pulse is the stimulation pulse provided to the heart. Thus, an APULSE triggers the generation of an A-Pulse.)
MODE_CH: A mode change signal that resets the PVC logic when changing modes.
INIT A signal used to initialize the pacemaker logic (used for testing during manufacture).
PVC_OFF: A signal that turns all PVC options off. Thus, any PVC detected when this signal (digital logic level) is present (active) will be treated as an R-wave, causing the V-A timing of the pacemaker to be reset.
WAKE_UP: A signal that wakes up a microprocessor during the pacemaker's absolute refractory period. This signal occurs at the start of absolute refractory and begins with a V-pulse, an R-wave, or a PVC. In VDD and DDD pacing modes, this signal indicates that a ventricular event has just occurred.
PW: A signal that indicates an atrial event, such as a P-wave, has been detected. This signal has been processed by the refractory timing and atrial channel noise detection logic.
RW: A signal that indicates a ventricular event, such as an R-wave (which could end up, after further processing, as a PVC) has been detected. This signal has been processed by the refractory timing and ventricular channel noise detection logic.
CHA_V: A clock signal used to sample the detected PW and RW events. (In the preferred embodiment, this is a 3.91 ms clock.)
BAIL_OUT: A signal that causes the PVC options to be disabled after a programmed number of consecutive PVC's.
PVC_RESET: A signal that resets the PVC BAIL_OUT counter and logic.
PW_INT: A P-wave interrupt signal that is delivered to the pulse generator logic.
RW_INT: An R-wave interrupt signal that is delivered to the pulse generator logic.
PVC_INT: A PVC interrupt signal that is delivered to the pulse generator logic.
PVC_RESP: A signal that arms the PVC option response of PVC1, PVC2, or PVC3.
PVC_TERM: A signal (register bit) that enables the PVC termination option after a programmed number of PVC's.
D(7:0): A bidirectional data bus for use in reading or writing to the PVC control register.
R_W: A signal that indicates a read from register when high, and a write to register when low.
SELECT: A strobe signal used to latch data or enable read back of data from the PVC control register.
AWARN: A pulse signal (preferably of 3.91 ms) that occurs just prior to APULSE.
BYPASS_A: A signal that indicates to bypass the atrial runaway protection briefly for the PVC2 responses.
E_VVI: A signal that causes a mode change to Emergency VVI mode. This signal resets the PVC logic and the PVC control register.
VWARN: A pulse (preferably of 3.91 ms) that occurs just prior to generating V-Pulse. This signal is used to reset the PVC_RESP and BAIL_OUT Counter when the pacemaker is in the VDD mode.
P_ARM: A signal (PVC control register bit) that forces the PVC2 option to be rearmed only with a P-wave.
PVC2_OFF: A signal that disables further PVC2 responses until a P-wave is sensed.
$V_{DD}$: A high logic level.
$V_{SS}$: A low logic level.

Many of the signals identified above are generated in conventional manner by the pacemaker control logic 12 (FIG. 2), such as PW, RW, WAKE_UP, CHA_V~, MODE_CH, INIT, AWARN, PNOISE, etc. Other signals are generated by the logic shown in FIGS. 10A-10C at appropriate times as explained below.

The operation of the circuit shown in FIGS. 10A-10C is controlled by the particular data word loaded into the PVC Control Register 120. This data word is received over a bidirectional data bus D(7:0), which data bus may be used to transfer other data, as required, throughout the control logic 12 (FIG. 2). Because the bus is bidirectional, data may be read from the PVC control register 120 or written thereto, as controlled by the R_W~ signal, and as timed with a SELECT strobe signal.

As presently configured, four data bits held in the PVC control register 120 are used to define its operating mode. These four bits are identified as B3, B2, B1 and B0. (The other bits, B7, B6, B5 and B4 may be used for other control purposes, not relevant to this invention, or may be maintained as spares for future use.) FIG. is a table that defines the options available by selectively setting these first four control bits. As shown in FIG. 11, bits B0 and B1 determine the particular PVC response that is to be provided. If both B0 and B1 are "0", all PVC responses are disabled, meaning no PVC response is generated (i.e., the PVC_OFF signal is generated). Thus, any ventricular signals sensed during this time (PVC_OFF active) are treated as R-waves, and the pacemaker responds accordingly. Other combinations of the bits B0 and B1 define three different PVC options, identified as PVC1, PVC2 or PVC3. More options are possible, of course, by using an additional bit (such as B4) to define the combinations. For purposes of FIG. 10A-10C, the first PVC option, PVC1, is a +PVARP on PVC. The second PVC option, PVC2, is A PACE ON PVC, and the third PVC option, PVC3, is a DVI on PVC. The operation of these three different options has been described previously. Conventional logic gates are used to monitor the various combinations of bits B0 and B1 in order to generate the signals PVC1, PVC2, and PVC3 in accordance with the pattern shown in FIG. 11.

The bit B2 is used to turn OFF or ON the PVC_TERM option. As defined above, PVC_TERM relates to the PVC termination option of the present invention. When ON, any PVC response invoked is terminated after a programmed number of cycles, as explained above in connection with FIG. 9. Bit B3 is used as the P_ARM signal. When active, the P_ARM signal forces the PVC2 option (A PACE ON PVC) to be rearmed only with a P-wave. When not active, the P_ARM signal disables such arming.

In FIG. 10A, a flip-flop circuit 101 generates the PNOISE signal whenever noise detection logic 100 determines that atrial activity has been sensed during the relative portion of the atrial refractory period. This flip-flop circuit 101, which may be a flip-flop that is clocked by the CHA_V~ clock signal, as well as the noise detection logic 100, preferably form part of the pacemaker's control logic 12 used during operation of the pacemaker.

Figure 12A:
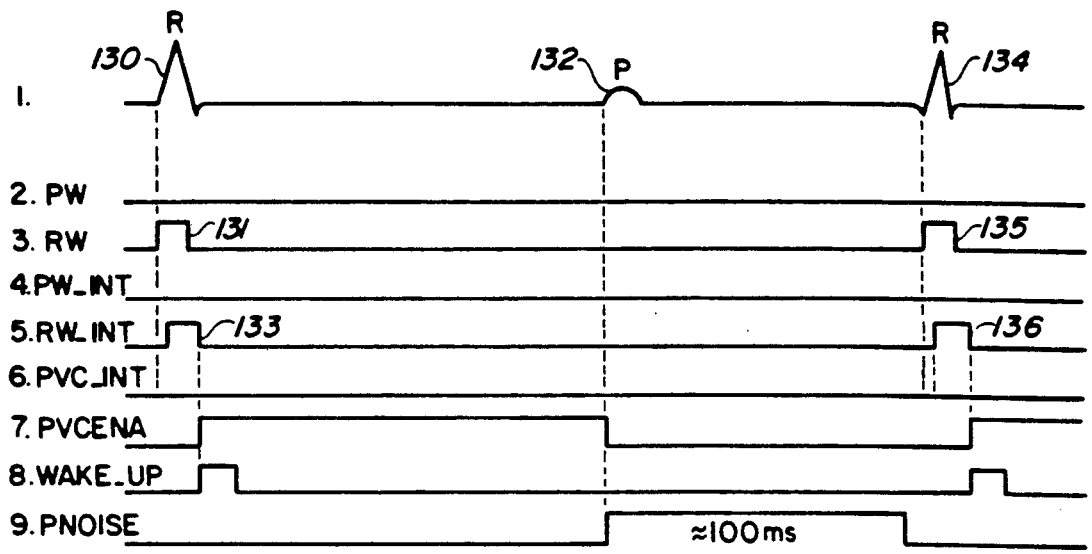

The basic operation of the circuit shown in FIGS. 10A-10C, given the signal definitions above, is better understood with reference to the signal timing diagrams shown in FIGS. 12A-12D, which signal timing diagrams show representative situations that may occur. Referring to FIG. 12A, for example, a situation is shown where the +PVARP ON PVC response is ON (i.e., PVC1 has been selected). The top waveform shows the ECG cardiac activity, i.e., an R-wave 130, followed by a P-wave 132 that occurs during PVARP, and followed by another R-wave 134. (It is to be emphasized that the timing diagrams shown in FIGS. 12A-12D are not drawn to scale.) The P-wave 132 is not sensed, because it occurs during PVARP. Hence, the second line, which shows the signal PW (which signal, as indicated above, indicates that a P-wave has been detected as processed through the pacemaker's conventional refractory timing and atrial channel noise detection logic), does not indicate the sensing of a P-wave. The R-waves, as shown on the third line of FIG. 12A, are sensed, as indicated by the pulses 131 and 135. Because no P-waves are sensed, there is no need to interrupt the P-wave pulse generator logic. Hence, no PW_INT signal is generated (fourth line of FIG. 12A). Note from FIG. 10A, that the PW_INT signal is generated by flip-flop 103 within one clock cycle (CHA_V~) after a PW signal is present. However, because the R-waves are sensed, the RW_INT signal pulses 133 and 136 are generated (fifth line) for the purpose of interrupting the R-wave generator logic. The RW_INT signal is generated by flip-flop 104 within one clock cycle (CHA_V~) after the occurrence of the RW signal. The setting of either flip-flop 104 (RW INT) or flip-flop 103 (PW_INT) causes flip-flop 102 to be clocked. Further, the WAKE UP signal (which, as indicated above, for VDD or DDD modes, indicates that a ventricular event has just occurred) is applied to the reset terminal of flip-flop 102 to ensure that flip-flop 102 is reset at this time. When flip-flop 102 is reset, or during other conditions (PVC_OFF or PVC2_OFF), a signal PVCENA (seventh line of FIG. 12A) is generated. This signal, when active, enables the PVC options. Hence, if another R-wave is sensed while PVCENA is active, such R-wave would be interpreted as a PVC. This occurs because with PVCENA active, the next RW signal is directed to flip-flop 105, rather than flip-flop 104, because of NAND gates 109a and 109b. That is, with PVCENA active, the next RW signal would be blocked from being applied to the "D" input of flip-flop 104 by NAND gate 109a, but would be allowed to be applied to the "D" input of flip-flop 105 through NAND gate 109b. Such action would cause the PVC_INT signal (sixth line of FIG. 12A) to be generated within one clock cycle. The PVC₁₃INT signal, in turn, would set latch 110, thereby generating the PVC_RESP signal, which signal arms the selected PVC option, i.e., either PVC1, PVC2 or PVC3.

The PVCENA signal, however, for the situation shown in FIG. 12A, remains active only until the occurrence of the PNOISE signal (indicating a P-wave, or other atrial activity, was sensed during the relative portion of the atrial refractory period). The PNOISE signal causes flip-flop 102 to toggle, thereby forcing PVCENA to an inactive state. Hence, in effect, the occurrence of PNOISE cancels any PVC response, because any subsequent RW signal is interpreted as an R-wave (causing flip-flop 104 to generate the RW_INT signal), and not as a PVC (with flip-flop 105 generating the PVC_RESP signal).

If an RW signal were to occur while the PVCENA signal were active, then the PVC_INT signal would be generated. The PVC_INT signal remains active, i.e., latch 110 remains set, until a BAIL_OUT signal or a PVC_RESET signal causes latch 110 to be reset. A BAIL_OUT signal is generated as shown in FIG. 10B. The PVC_INT signal, a pulsed signal having a duration equal to one clock cycle of the CHA_V~ clock signal (and generated by flip-flop 105 as shown in FIG. 10A for each occurrence of a PVC), is applied to flip-flops 106 and 107. Flip-flops 106 and 107 are configured as counter circuit adapted to count to four. Thus, after four successive PVC's (without flip-flops 106 and 107 being reset), an output signal is generated by flip-flop 107 indicating that four successive PVC's have occurred. If the PVC_TERM bit is set (bit B2 of the PVC Control Register 120), then flip-flop 108 causes a BAIL OUT signal to be generated, which BAIL_OUT signal resets latch 110 (FIG. 10A), thereby terminating the PVC response after the occurrence of four successive PVC's.

Those skilled in the art will appreciate that a count of four PVC's, as is detected by the counter circuit comprising flip-flops 106 and 107, is only exemplary. Any desired count could be just as easily detected by a suitable counter circuit adapted to count the PVC_INT pulse signal. If desired, for example, a programmable counter could be fashioned, with the count of the counter being set by, e.g., the unused bits, B5-B7 held in the PVC Control Register 120.

As also shown in FIG. 10A, a PVC_RESET signal also terminates the PVC_RESP mode, i.e., also resets latch 110. A PVC_RESET signal is generated by OR gate 109C upon the occurrence of any of four possible events: (1) the detection of either a P-wave or an R-wave, as manifest by the setting of flip-flops 103 or 104, respectively; (2) the occurrence of both an AWARN signal and the absence of an BYPASS_A signal (i.e., the presence of a BYPASS_A~ signal, where "~" means the inverse signal, or an active low signal); (3) the occurrence of a pacemaker mode change, thereby creating a MODE_CH signal; or (4) the occurrence of a VWARN signal, indicating a V-pulse will be generated in one clock cycle (e.g., 3.91 milliseconds, for the embodiment shown).

Figure 12B:
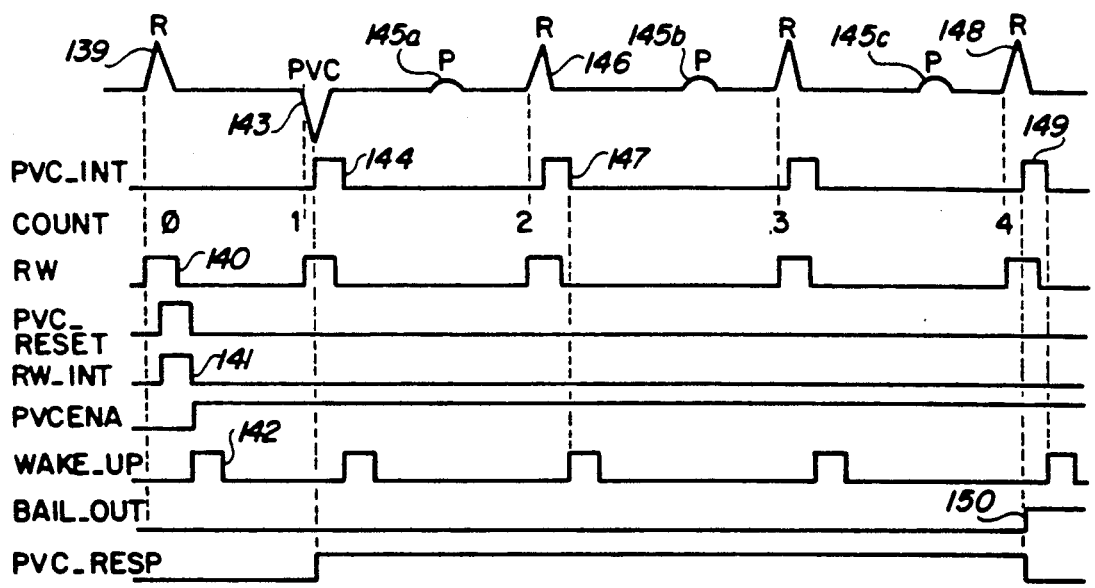

FIG. 12B shows a timing waveform diagram illustrating the operation of the circuit of FIGS. 10A-10C for a situation when the +PVARP response is selected (PVC1), and a PVC is detected. As shown in FIG. 12B, the occurrence of an R-wave 139 causes the RW pulse signal to be generated in conventional pacemaker fashion. The RW pulse, triggers flip-flop 104 to generate the RW_INT signal as described above. The detection of the R-wave also causes a WAKE_UP signal pulse 142 to be generated. The WAKE_UP signal resets flip-flop 102, causing the PVCENA signal to go active (high), thereby causing any subsequent R-waves, without an intervening P-wave, to be interpreted as a PVC. For the situation shown in FIG. 12B, the next ventricular event is a PVC 143. Because the PVCENA signal is active, this event is coupled to flip-flop 105, causing a first PVC_INT pulse 144 to be generated. This first PVC_INT pulse also sets latch 110, causing the PVC_RESP signal to go active (high), thereby arming the selected PVC response (in this instance, PVC1). A first P-wave 145a that follows the PVC 143 is not detected because it occurs during the extended PVARP period invoked by the PVCI response. Hence, a next R-wave 146, is also interpreted as a PVC, causing a second PVC_INT pulse 147 to be generated. This process continues up until a fourth R-wave 148 is sensed. This fourth R-wave 148 causes a fourth PVC_INT pulse 149 to be generated, which pulse causes the PVC counter (comprising flip-flops 106 and 107) to reach its terminal count, thereby generating the BAIL_OUT signal 150. The BAIL_OUT signal 150, in turn, resets latch 110, and terminates the PVC response, i.e., forces the PVC_RESP signal to go inactive (low).

FIG. 12C illustrates operation of the circuit an R-wave interpreted as a PVC occurs during a BAIL_OUT response, i.e., when the BAIL_OUT signal is active. The operation of the circuit under these conditions is that of normal PVARP and VA timing with PVC_RESP low (inactive). (Note, PVARP means "post ventricular atrial refractory period".)

FIG. 12D illustrates operation of the circuit shown in FIGS. 10A-10C for the situation where a P-wave 160 occurs during alert (after a normal PVARP). Such occurrence causes flip-flop 103 to generate the PW_INT signal, which in turn generates a PVC_RESET pulse. The PVC_RESET pulse causes a new Bail-Out sequence to begin. That is, the counter 106/107 is reset and begins counting over again up to the prescribed number.

FIG. 13 is a functional block diagram depicting an alternative embodiment of the present invention that recognizes true PVC's by monitoring the morphology (e.g., shape) of the R-wave and/or measuring/monitoring selected time intervals associated with atrial and/or ventricular events. A sense amplifier 20' senses ventricular depolarization in conventional manner. The output of amplifier 20' is sampled, using sample and hold (S/H) circuit 182, at appropriate intervals, e.g., every 1-10 milliseconds. Each sample is then digitized using analog-to-digital (A/D) converter 184, and the resulting digital signal (digital word) is presented to processor 190. Processor 190 compares each digitized sample thus generated with a corresponding previously generated or defined digitized sample of a PVC stored in memory 188. If a sufficient number of the samples compare favorably, i.e., are approximately the same, then the processor assumes that the morphology of the sensed R-wave is approximately the same as the morphology of a PVC, as defined by the stored sample values of a representative PVC stored in memory 188. Hence, the processor signals the pulse generator and control logic 12' that a PVC has been detected, whereupon an appropriate PVC response can be initiated, such as +PVARP on PVC, or DVI on PVC.

The circuit of FIG. 13 also senses atrial activity using atrial sense amplifier 18', and provides A-pulses through drive amplifier 14', as well as V-pulses through drive amplifier 24', in conventional manner. The processor 190 is further adapted to measure and monitor selected time intervals associated with these sensed atrial and/or ventricular events, and to use such measurements as a further indication of whether a PVC has in fact occurred, and if so, whether a PVC response should be triggered.

Figure 14:
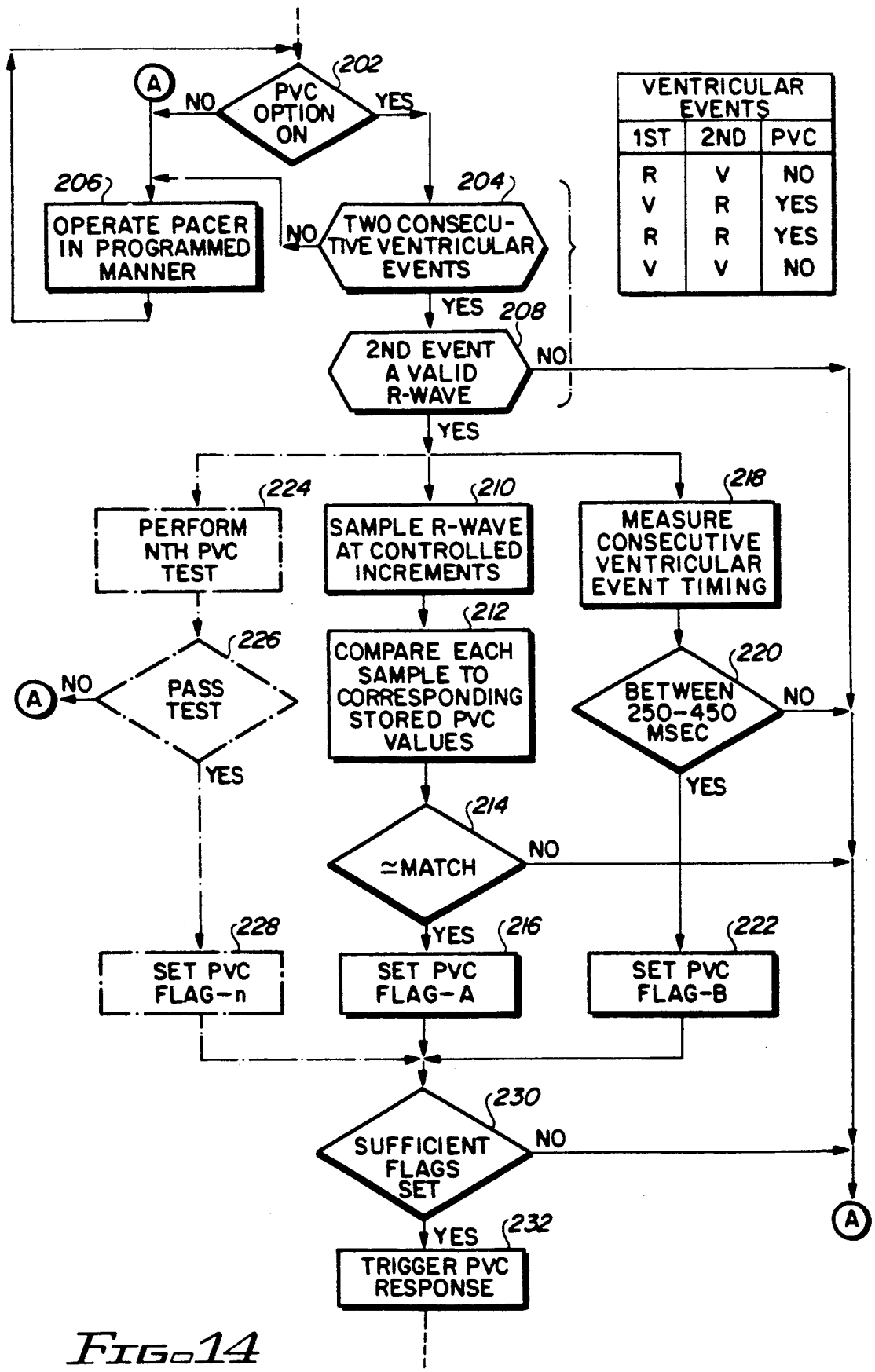
FIG. 14 is a simplified flowchart illustrating one manner in which the processor included in FIG. 13 may operate in order to recognize a PVC.

FIG. 14 is a simplified flowchart illustrating one manner in which the processor 190 included in FIG. 13 may operate in order to recognize a PVC. As shown in that flowchart, if a PVC option mode is ON (block 202 in FIG. 14), then a determination is made, at block 204, as to whether two consecutive ventricular events, e.g., R-waves, have occurred without an intervening sensed or paced atrial event. If not, a PVC has not occurred, and the normal programmed operation of the pacemaker continues (block 206). If the second ventricular event is a valid R-wave (block 208), i.e., not just noise, then a PVC may have occurred. Truth table 205, included in the upper right corner of FIG. 14, defines what normally determines whether a PVC has occurred. However, to further evaluate whether a true PVC has actually occurred in accordance with the present invention, any one, or any combination, of a several possible additional tests may be undertaken. Because these tests are performed by the processor 190, typically based on digital data presented to the processor, these various tests may be carried out in "parallel". (Those skilled in the art will recognize, of course, that the processor, unless comprising multiple processors, actually only performs one processing step at any instant of time. But with the processor speeds currently available, it is possible for single processing steps for each test to be performed, by jumping from one test to another as required, in such a rapid manner that it appears that all of the various tests are performed in parallel.)

A first test that may be performed, as shown in FIG. 14, is to compare the morphology of the sensed R-wave with the morphology of a stored PVC, as described above. Essentially, this involves sampling the R-wave at controlled increments (block 210); comparing each sample to corresponding stored PVC samples (block 212); determining if a match exists for corresponding samples (block 214); and, if so, setting a PVC flag, identified as Flag-A (block 216). A second test involves measuring the time interval between the two consecutive ventricular events (block 218). Such time interval measurement is then compared to a range of specified times, e.g., 250 to 450 milliseconds, where most PVC's would be expected to be sensed (block 220). If the test passes (block 220), then a second PVC flag, Flag-B, is set (block 222). Additional tests may also be performed, if desired, as represented by the dotted lines in FIG. 14 (blocks 224, 226, 228). If these tests are passed, meaning that each test points towards the occurrence of a PVC, then an appropriate flag, Flag-n, is set for each test, where the integer n represents the flag for the nth test. Once all the desired tests have been performed, a determination is made as to whether a sufficient number of flags have been set (block 230). If so, an appropriate PVC response can be triggered (block 232), such as any of the responses previously described.

In accordance with this method of detecting a PVC, the setting of any number of flags can advantageously be selected to indicate the occurrence of a PVC, thereby providing a means for adjusting the probability that a true PVC has occurred. For example, if four tests are performed, the setting of any two flags from the four tests may be considered sufficient evidence that a PVC has occurred. Alternatively, for a more sure indication of a PVC, the setting of any three flags of the four tests may be selected. Similarly, if three tests are performed, the setting of any two flags from the three tests may be considered sufficient indication of a PVC. If two tests are performed, the setting of either flag can be used as a PVC-indicating criteria; or the setting of both flags may be required. If only a single test is performed, then the setting of the flag for that test provides the PVC-occurrence criterion. In this manner, a great deal of flexibility is provided in the manner in which a true PVC is detected.

As described above, it is thus seen that the present invention provides a safe and reliable circuit that can be used within an implantable pacemaker to improve the ability of the pacemaker to distinguish true PVC's from other events that prior pacemakers would have interpreted as PVC's, but were not. Further, once a true PVC has been detected, and a prescribed PVC response mode is initiated, the present invention prevents such PVC response mode from becoming stuck. Such feature, in accordance with one embodiment of the invention, allows the PVC response of the pacemaker to continue for only a prescribed number of consecutive cardiac cycles, which prescribed number may be programmably selected. As a result, the prescribed PVC response minimizes the likelihood of triggering a pacer mediated tachycardia.

Further, it is seen that the invention described above advantageously provides a PVC detecting and response means that provides a selectable PVC response only if certain events occur that are strongly indicative of a true PVC, and that provides no PVC response for events only suggestive of the possibility of a PVC. Hence, the present invention recognizes, unlike the current teachings of the PVC-responsive pacemaker art, that the best PVC response may frequently be no response, i.e., no response different from the normal operation of the pacemaker. Coupled with this recognition is the additional recognition that if a PVC response is provided by the pacemaker, such response should only continue for a short time, thereby preventing the possibility that the PVC response might become stuck.

While the invention described herein has been described with reference to particular embodiments and applications thereof, numerous variations and modifications could be made thereto by those skilled in the art without departing from the spirit and scope of the invention as claimed.

What is claimed is:

1. In an implantable pacemaker having means for sensing atrial and ventricular events, means for generating an atrial stimulation pulse, means for generating an atrial refractory time interval having a relative refractory portion wherein sensed atrial activity is considered as atrial noise and not as a valid atrial event, and means for detecting apremature ventricular contraction (PVC) and responding thereto in a prescribed manner, electornic circuit means for preventing said PVC detecting means from responding to a false PVC comprising:
   means for generating a latched signal in the event atrial noise is sensed during said relative refractory portion of said atrial refractory time interval;
   means responsive to said latched signal for causing said PVC detecting means to assume a disabled state, said disabled state continuing until the first occurrence thereafter of a prescribed re-enabling event; and
   means responsive to said prescribed re-enabling event for enabling said PVC detecting means;
   a PVC thereby not being detectable by said PVC detecting means subsequent to the occurrence of atrial noise until said re-enabling event occurs.

2. The electronic circuit means as defined in claim 1 wherein said re-enabling event comprises a ventricular event, said ventricular event including an R-wave sensed by said pacemaker or the generation of a ventricular stimulation pulse by said pacemaker, whichever event occurs first after the generation of said latched signal.

3. The electronic circuit means as defined in claim 1 wherein the prescribed manner in which said pacemaker responds to the detection of a PVC comprises entering a PVC response mode, said pacemaker providing a specific response when in said PVC response mode aimed at preventing the occurrence of a pacemaker mediated tachycardia, said electronic circuit means further including means for terminating said PVC response mode in the event n consecutive cardiac cycles occur during said PVC response mode, where n is an integer greater than two, and a cardiac cycle is defined as the time interval between consecutive ventricular events.

4. The electric circuit means as defined in claim 3 wherein the integer n is programmably selectable from a range of integer values comprising three to ten.

5. A system for detecting premature ventricular contractions for use in an implantable, programmable, pacemaker comprising:
   detection means for detecting first and second ventricular events without an intervening atrial event;
   first means for testing the second detected ventricular event to determine if said second detected ventricular event exhibits a first specified criterion of a premature ventricular contraction (PVC);

second means for testing the second detected ventricular event to determine if said second detected ventricular event exhibits a second specified criterion of a PVC;

decision means coupled to said first and second test means for determining whether a selected one of said first or second specified criterion is exhibited in said second detected ventricular event, and if so for generating a PVC detection signal indicating that a PVC has occurred;

PVC response means responsive to said PVC detection signal for triggering a selected PVC response of said pacemaker; and means for disabling said detection means upon the occurrence of prescribed atrial activity and re-enabling said detection means upon the occurrence of a prescribed enabling event.

6. The PVC detection system of claim 5 further including third means for testing a selected one of said second detected ventricular event or detected ventricular events subsequent to said second detected ventricular event to determine if said selected one of said second or subsequent ventricular events exhibit third specified criterion; and further wherein said decision means is for determining whether a selected combination of said first, second, or third criteria are exhibited in said selected one of said second or subsequent sensed ventricular events, and if so for generating said PVC detection signal.

7. The PVC detection system of claim 5 further including means for automatically terminating the PVC response triggered by said PVC response means if a prescribed number of consecutive ventricular events occur.

8. A method for preventing a false premature ventricular contraction (PVC) response of an implantable pacemaker, said pacemaker including means for detecting a PVC and providing a prescribed PVC response, said method comprising the steps of:

(a) disabling said PVC detecting means upon the occurrence of any atrial event that might possibly be a valid atrial event; and (b) re-enabling said PVC detecting means only upon the occurrence of a prescribed enabling event.

9. The method set forth in claim 8 wherein step (b) of re-enabling said PVC detecting means comprises re-enabling said PVC detecting means upon the occurrence of a ventricular event, said ventricular event including either an R-wave sensed by said pacemaker or a ventricular stimulation pulse generated by said pacemaker, whichever event occurs first after said PVC detecting means has been disabled.

10. The method set forth in claim 8 wherein step (a) of disabling said PVC detecting means includes sensing whether any atrial events occur during a relative portion of an atrial refractory time interval; assuming said sensed atrial events, if any, indicate a valid atrial event; and disabling said PVC detecting means in response to said sensed atrial events.

11. The method set forth in claim 10 further comprising the steps of:

(c) providing said prescribed PVC response of the pacemaker upon the detection of a PVC by said enabled PVC detecting means; and (d) automatically terminating said prescribed PVC response in the event n consecutive ventricular events are detected by said pacemaker's PVC detection means, where n is an integer greater than two.

12. The method set forth in claim 11 wherein step (d) includes selecting the integer n to be a desired value in the range of three to ten.

13. A method for automatically terminating a stuck premature ventricular contraction (PVC response of an implantable pacemaker comprising:

(a) sensing a PVC with PVC detection means;

(b) disabling said PVC detection means in the event an atrial event occurs early in a cardiac cycle at a time that only invalid atrial events are expected to occur, and re-enabling said PVC detection means upon the occurrence of a prescribed enabling event;

(c) enabling a PVC response mode of said pacemaker in response to the sensing of a PVC with said PVC detection means;

(d) monitoring the number of cardiac cycles that occur while said PVC response mode is enabled; and (e) disabling said PVC response mode if the number of cardiac cycles occurring during said PVC response mode reaches n, where n is an integer greater than two.

14. The method set forth in claim 13 wherein the value of the integer n is programmable.

15. The method set forth in claim 14 wherein the value of the integer n is within the range of three to ten.

16. The method set forth in claim 13 wherein the value of the integer n is equal to four.

17. In an implantable programmable pacemaker having means for sensing a premature ventricular contraction (PVC) and responding thereto with a prescribed response, PVC response termination means for terminating the prescribed response of said PVC sensing means in the event said prescribed response becomes stuck, said PVC response termination means comprising:

means for enabling a PVC response mode of said pacemaker in response to the sensing of a PVC by said PVC sensing means, said means for enabling a PVC response mode including means for disabling said PVC sensing means in the event an atrial event occurs early in the cardiac cycle at a time that only invalid atrial events, such as noise, are expected to occur, thereby minimizing the likelihood that a false PVC will be detected by the PVC sensing means of the pacemaker;

means for monitoring the number of cardiac cycles that occur while said PVC response mode is enabled; and means for disabling said PVC response mode if the number of cardiac cycles occurring during said PVC response mode reaches n, where n is an integer greater than two.

18. The PVC response termination means as set forth in claim 17 wherein the value of the integer n is programmable.

19. The PVC responsive termination means as set forth in claim 17 wherein said means for enabling a PVC response mode includes means for generating a pulsed signal upon the sensing of each PVC.

20. The PVC response termination means as set forth in claim 19 wherein said means for monitoring the number of cardiac cycles that occur while said PVC response mode is enabled comprises a counter circuit adapted to count the number of consecutive cardiac cycles during which a PVC occurs while said pacemaker is operating in said PVC response mode.

21. The PVC response termination means as set forth in claim 17 wherein the prescribed response of said pacemaker to a detected PVC comprises one of a plurality of PVC responses that may be programmably selected.

* * * * *